(12) United States Patent
Hu et al.

(10) Patent No.: US 9,040,081 B2
(45) Date of Patent: May 26, 2015

(54) USE OF LIPID CONTAINING PARTICLES COMPRISING QUILLAJA SAPONINS FOR THE TREATMENT OF CANCER

(75) Inventors: Kefei Hu, Uppsala (SE); Bror Morein, Uppsala (SE)

(73) Assignee: DUECOM (SE)

( * ) Notice: Subject to any disclaimer, the term of this patent is extended or adjusted under 35 U.S.C. 154(b) by 1184 days.

(21) Appl. No.: 12/515,684

(22) PCT Filed: Nov. 20, 2007

(86) PCT No.: PCT/SE2007/050878
§ 371 (c)(1),
(2), (4) Date: Dec. 8, 2009

(87) PCT Pub. No.: WO2008/063129
PCT Pub. Date: May 29, 2008

(65) Prior Publication Data
US 2010/0119591 A1    May 13, 2010

Related U.S. Application Data

(60) Provisional application No. 60/866,445, filed on Nov. 20, 2006.

(51) Int. Cl.
| | | |
|---|---|---|
| *A61K 9/48* | (2006.01) | |
| *A61K 39/00* | (2006.01) | |
| *A61K 31/704* | (2006.01) | |
| *A61K 39/39* | (2006.01) | |

(52) U.S. Cl.
CPC ........... *A61K 39/0011* (2013.01); *A61K 31/704* (2013.01); *A61K 39/39* (2013.01); *A61K 2039/55555* (2013.01); *A61K 2039/55577* (2013.01)

(58) Field of Classification Search
None
See application file for complete search history.

(56) References Cited

U.S. PATENT DOCUMENTS

| 6,375,945 B1 | 4/2002 | Boon et al. |
|---|---|---|
| 6,846,489 B1 | 1/2005 | Garcon et al. |
| 2005/0175623 A1* | 8/2005 | Wang .................... 424/184.1 |

FOREIGN PATENT DOCUMENTS

| CA | 2572427 | | 1/2006 |
|---|---|---|---|
| EP | WO9611711 | * | 4/1996 |
| WO | WO9209589 | * | 6/1992 |
| WO | WO9221331 | * | 12/1992 |
| WO | WO-98/15287 A1 | | 4/1998 |
| WO | WO-98/56420 A1 | | 12/1998 |
| WO | WO-00/62800 A2 | | 10/2000 |
| WO | WO-2005/002620 A1 | | 1/2005 |

OTHER PUBLICATIONS

Mutation Research, 480-481 (2001) 219-229 by Trosko et al.*
"International Application Serial No. PCT/SE2007/050878, International Preliminary Report on Patentability mailed Mar. 5, 2009", 14 pgs.
"International Application Serial No. PCT/SE2007/050878, International Search Report mailed Feb. 26, 2008", 9 pgs.
"International Application Serial No. PCT/SE2007/050878, Written Opinion mailed Jan. 16, 2009", 10 pgs.
Pearse, M. J., et al., "ISCOMATRIX® adjuvant for antigen delivery", *Advanced Drug Delivery Reviews*, 57, (2005), 465-474.
Sjölander, A., et al., "ISCOMs: an adjuvant with multiple functions", *Journal of Leukocyte Biology*, 64, (Dec. 1998), 713-723.
Skene, C. D., et al., "Saponin-adjuvanted particulate vaccines for clinical use", *Methods*, 40, (2006), 53-59.

* cited by examiner

*Primary Examiner* — Snigdha Maewall
(74) *Attorney, Agent, or Firm* — Schwegman Lundberg & Woessner, P.A.

(57) ABSTRACT

The present invention relates to the use of lipid containing particles, such as liposomes, iscom and/or iscom matrix and posintros, comprising at least one lipid and at least one saponin for the preparation of a pharmaceutical for the treatment of cancer. The saponins are preferably from *Quillaja Saponaria* Molina. Further, the particles are also delivery systems for one or several compounds for cancer treatment with complementary mechanisms. More, the invention discloses kit of parts comprising at least two parts, wherein one part comprising at least one saponin fraction which is hydrophobic having a killing effect on cancer cell; and the other part comprising at least one saponin fraction which is comparatively hydrophilic, stimulating and modulating the immune response.

8 Claims, 15 Drawing Sheets

Fig. 1.1
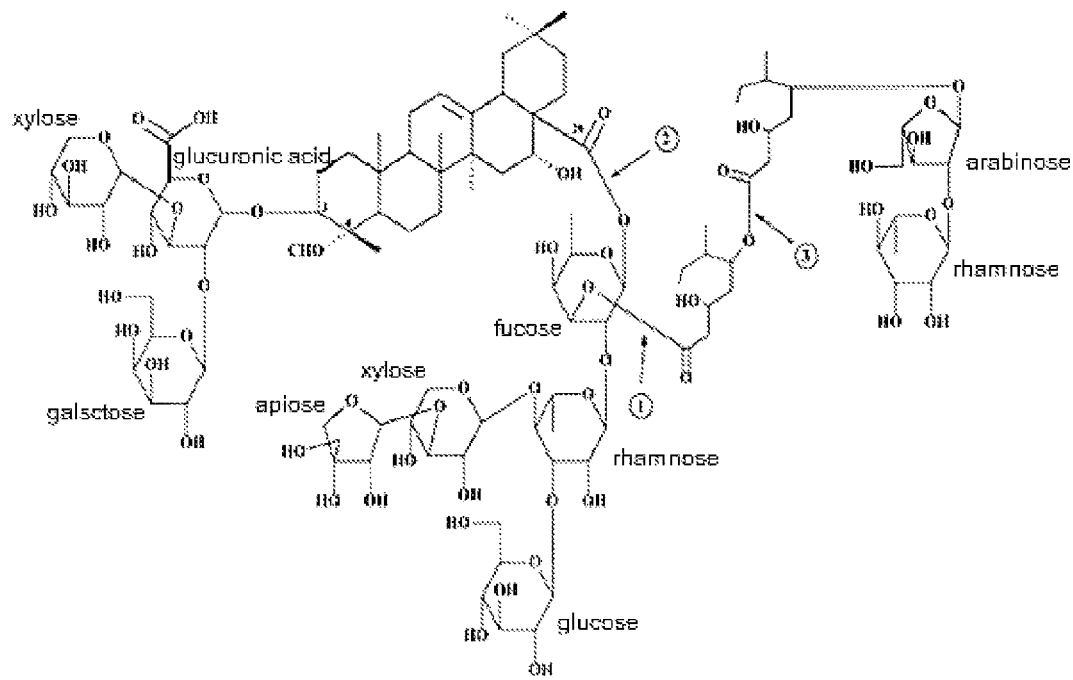
Fig. 1.2
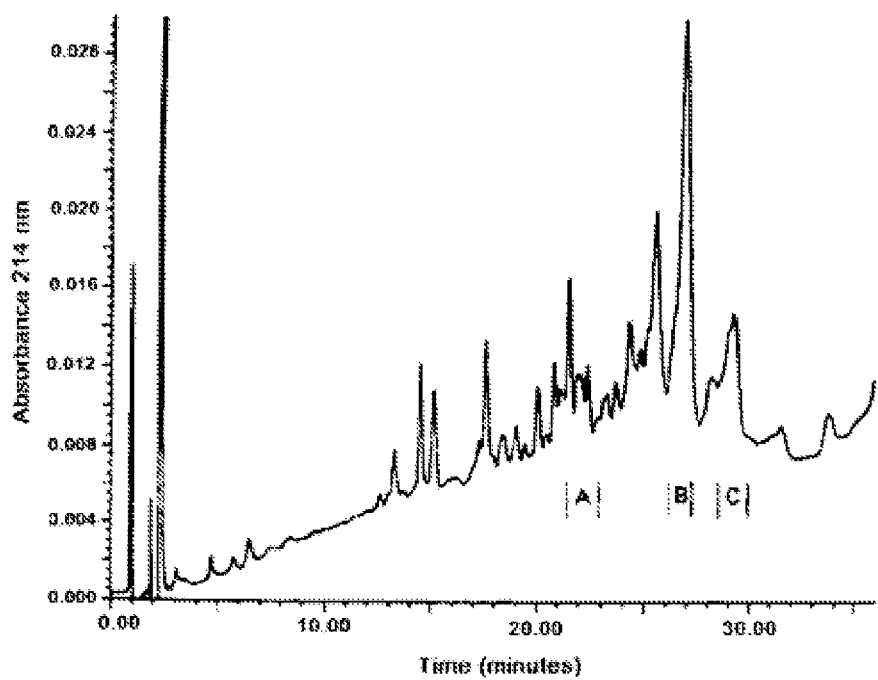

Fig. 1.3
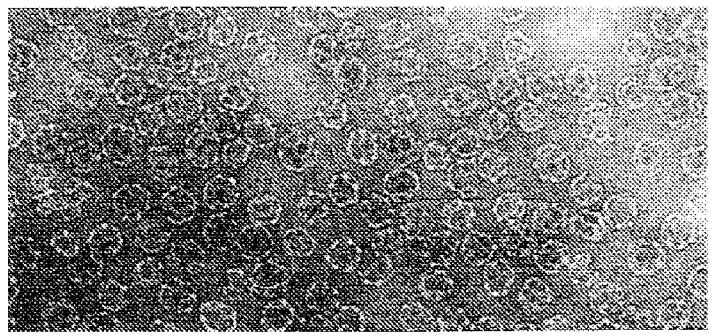
Fig. 2.1
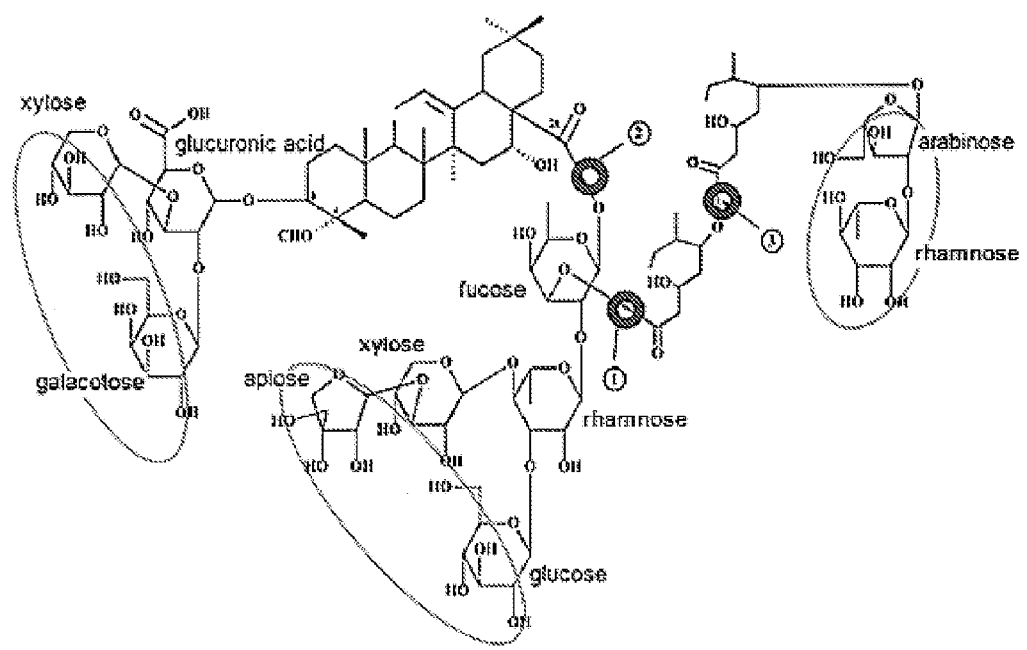

Fig. 3.1
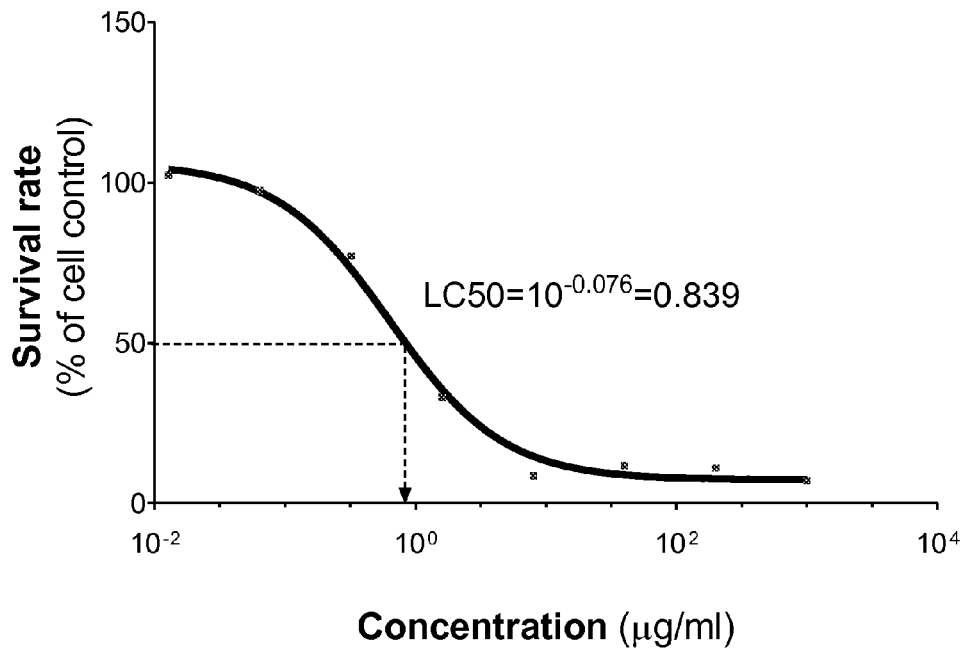
Fig. 3.2
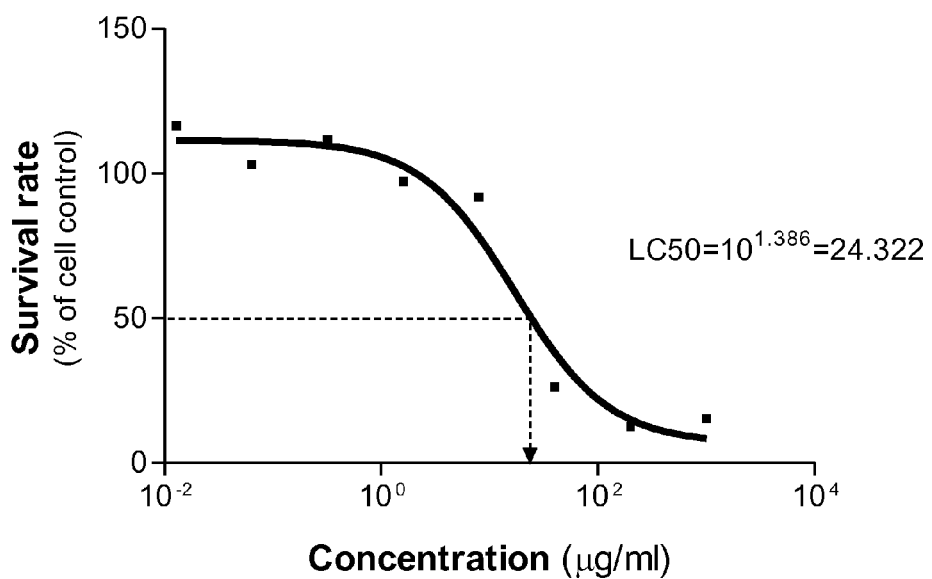

Fig. 4.1
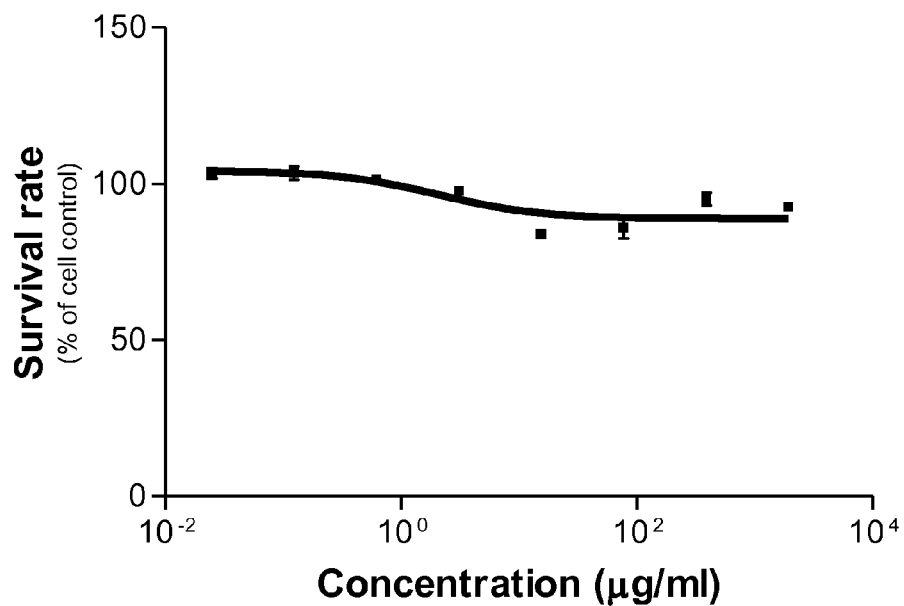
Fig. 4.2
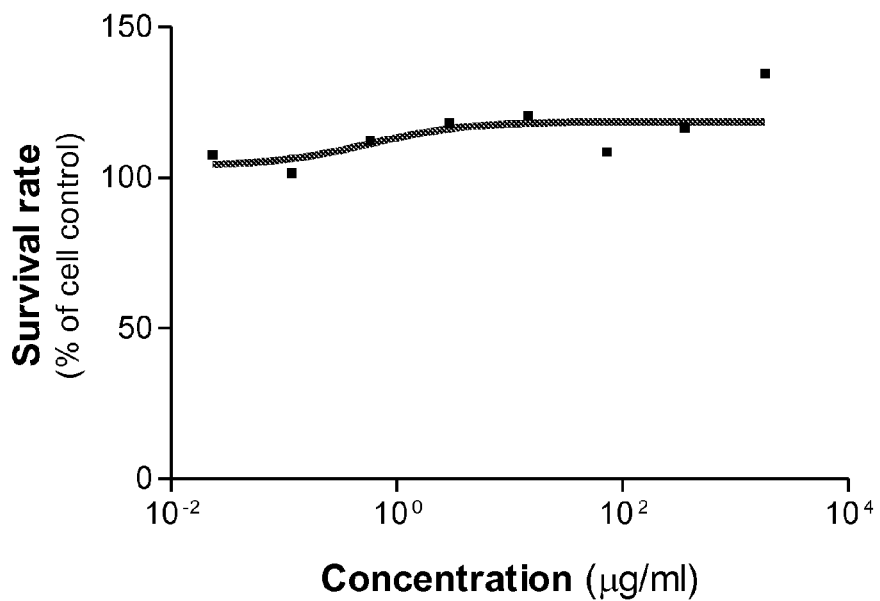

Fig 5.1
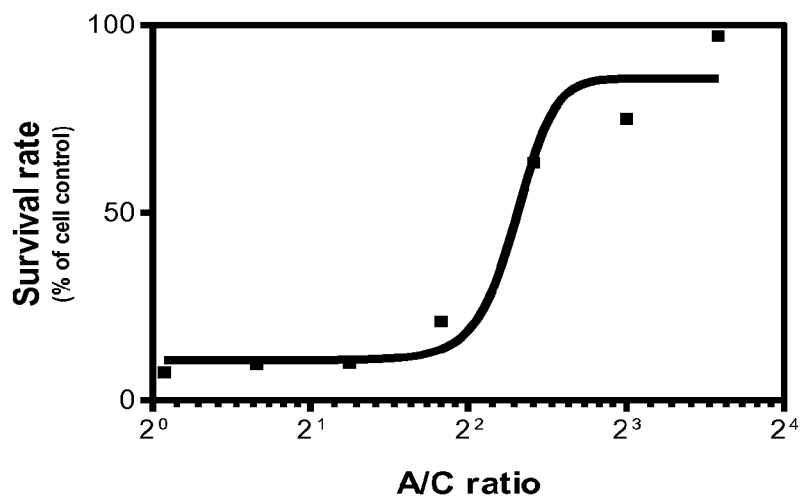
Fig. 6.1
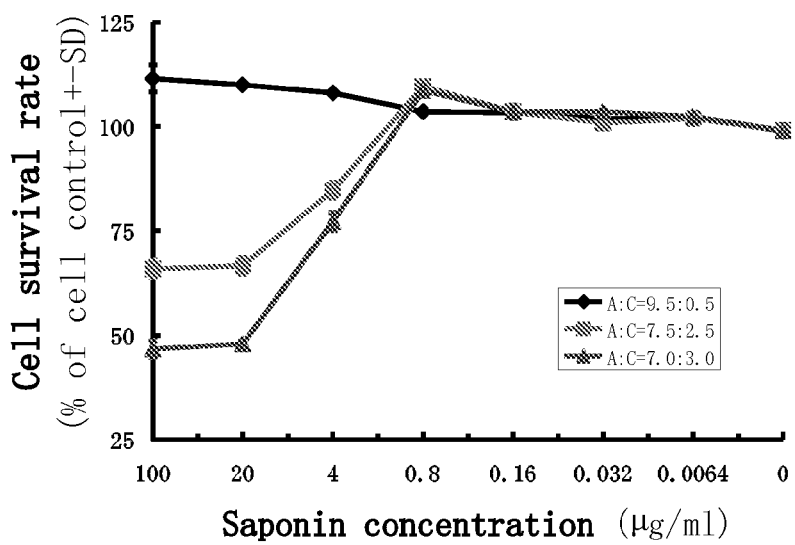

Fig. 6.2
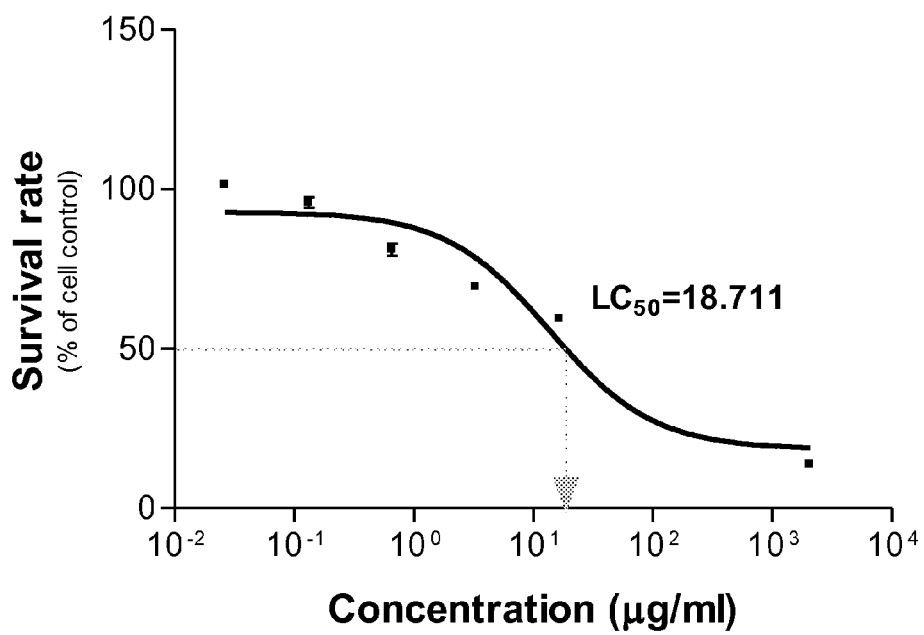
Fig. 6.3.
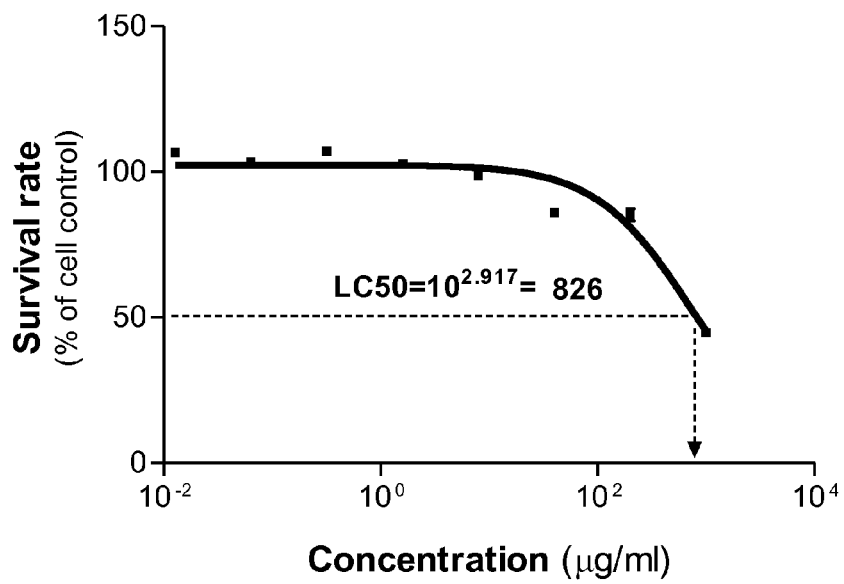

Fig. 6.4
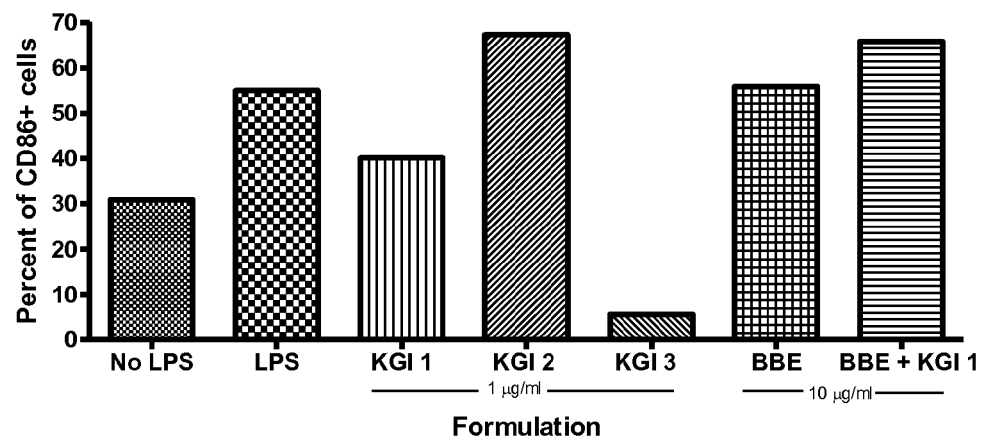
Fig. 7.1
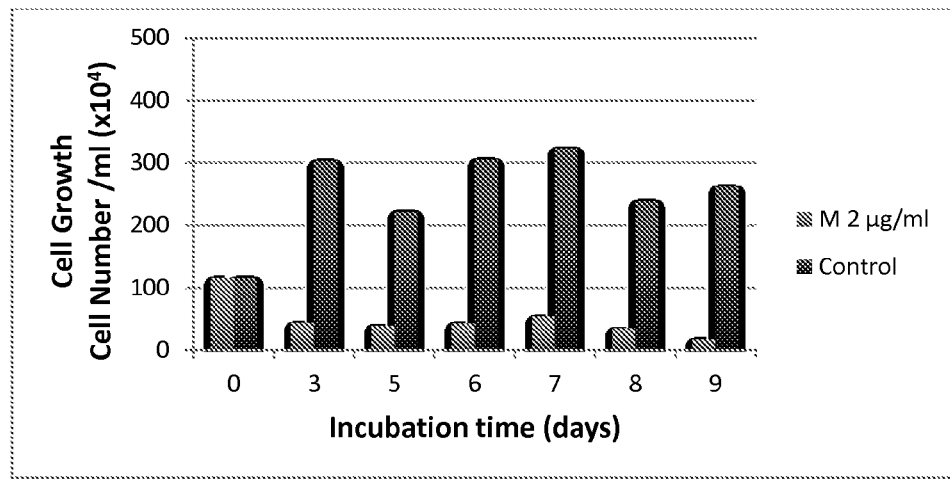

Fig 7.2
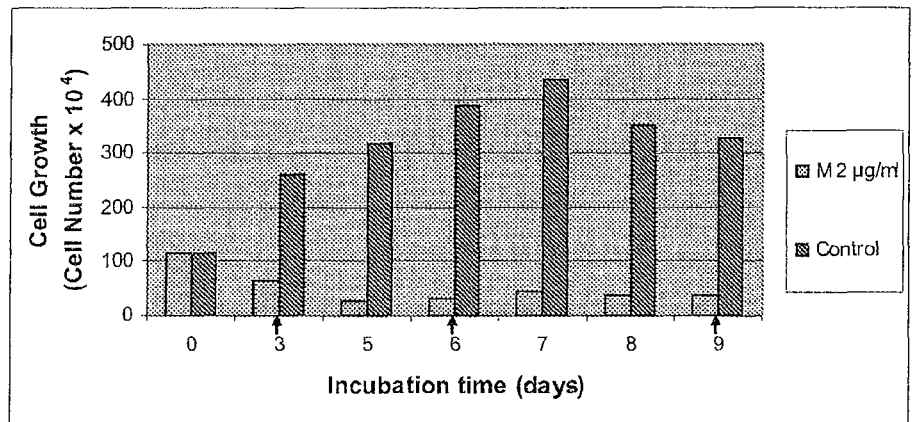
Fig. 7.3
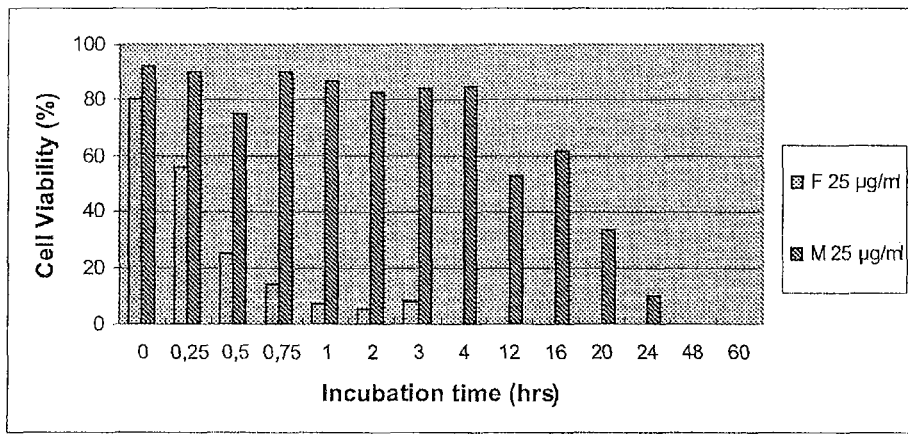
Fig. 7.4
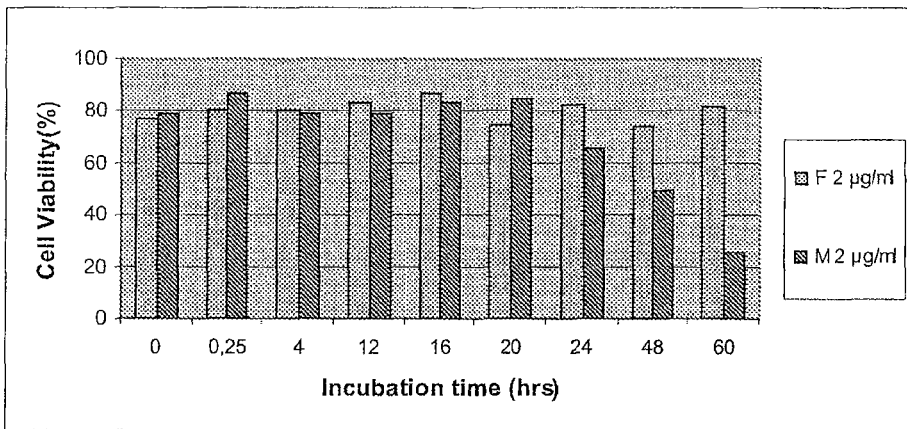

Fig 7.5.
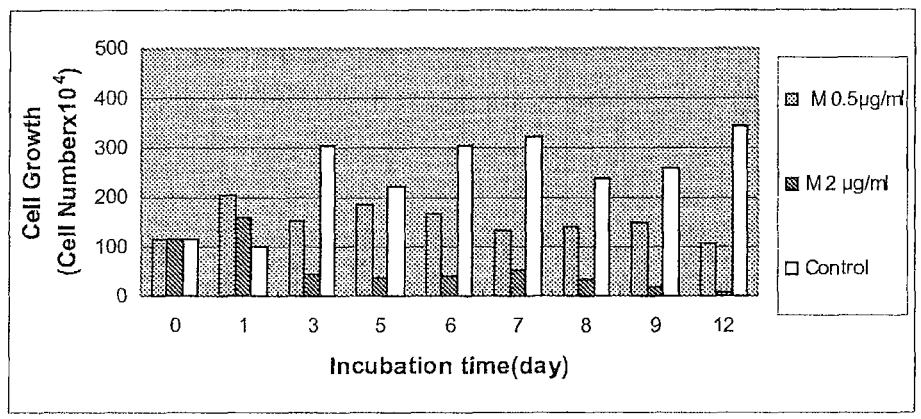
Fig. 7.6
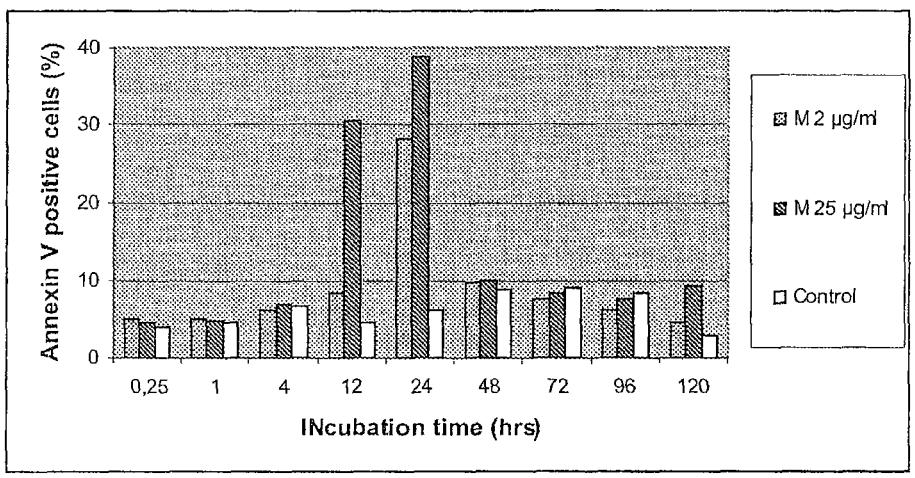
Fig. 7.7
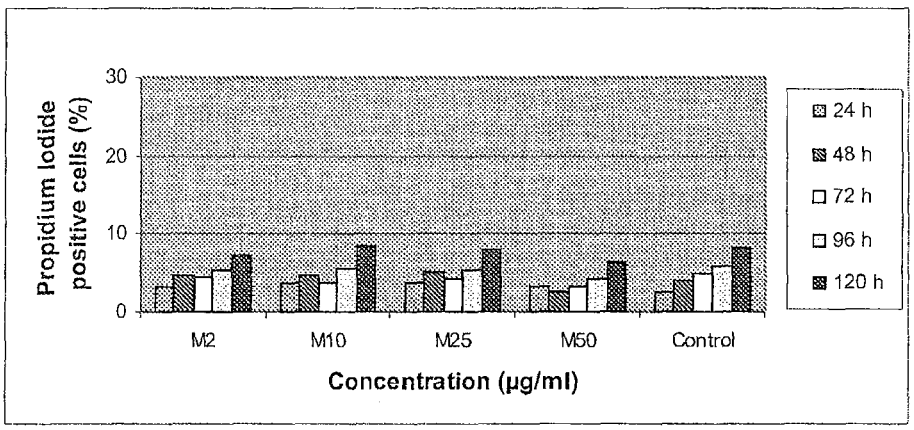

Fig. 7.8
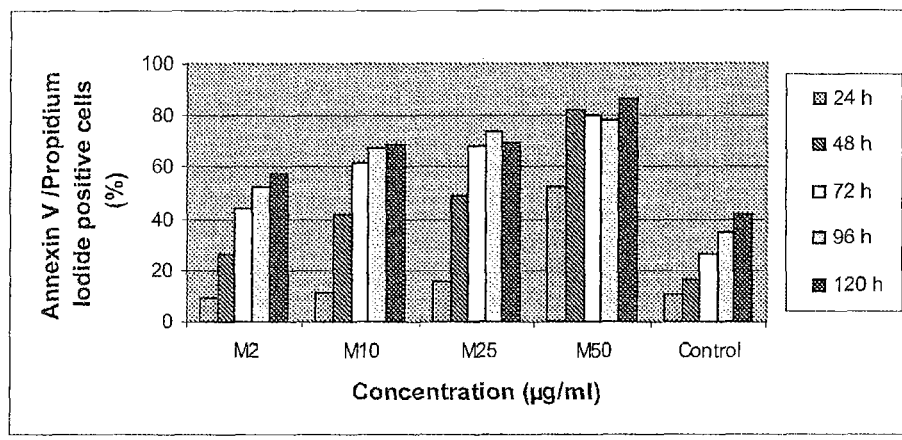
Fig. 8.1.
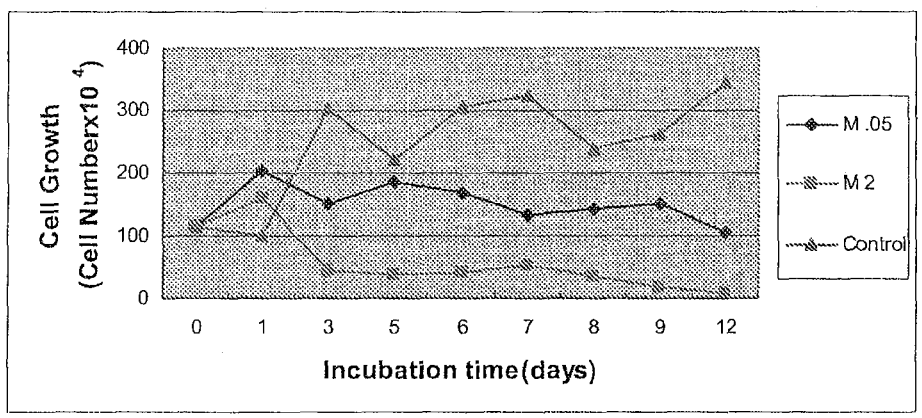
Fig. 8.2
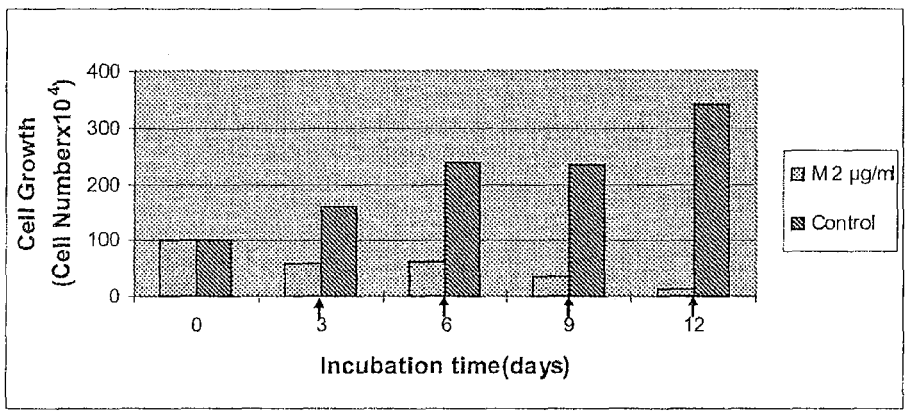

Fig. 9.1
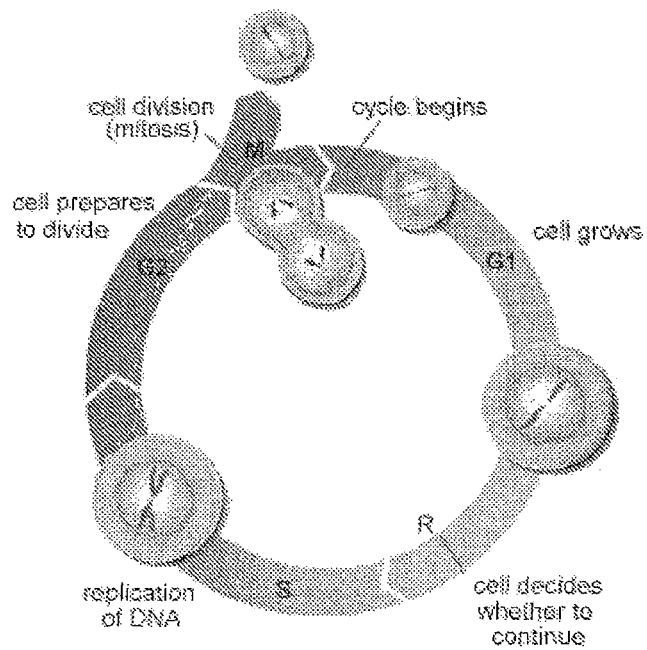
Fig. 9.2
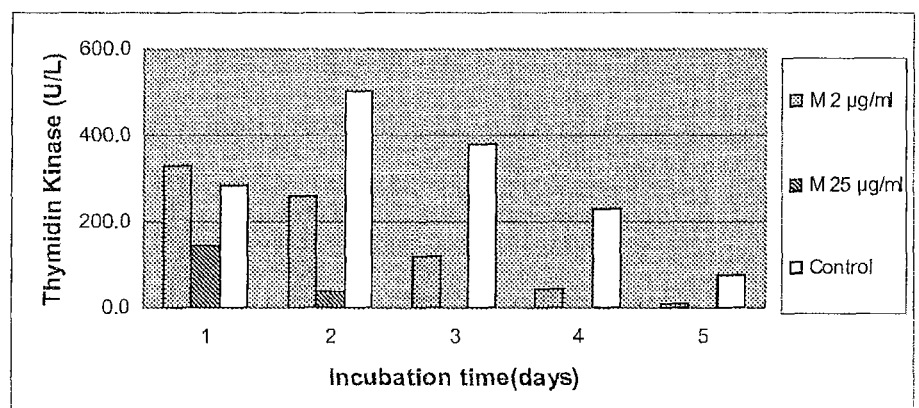

Fig. 9.3
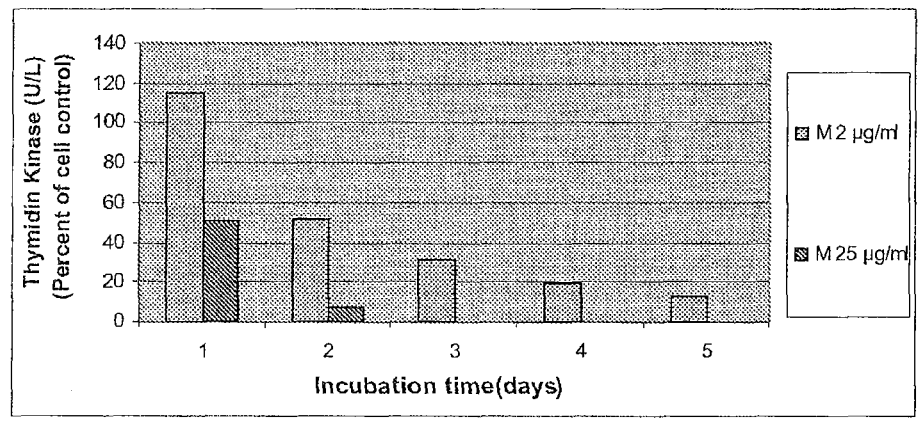
Fig. 9.4
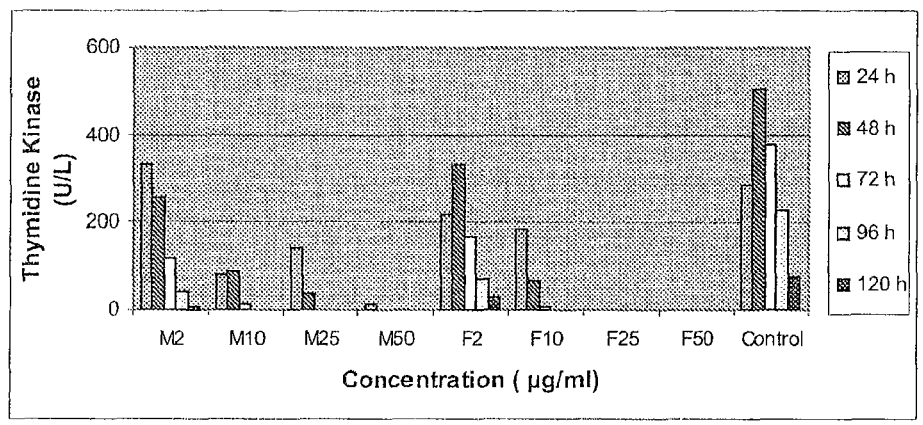
Fig. 9.5
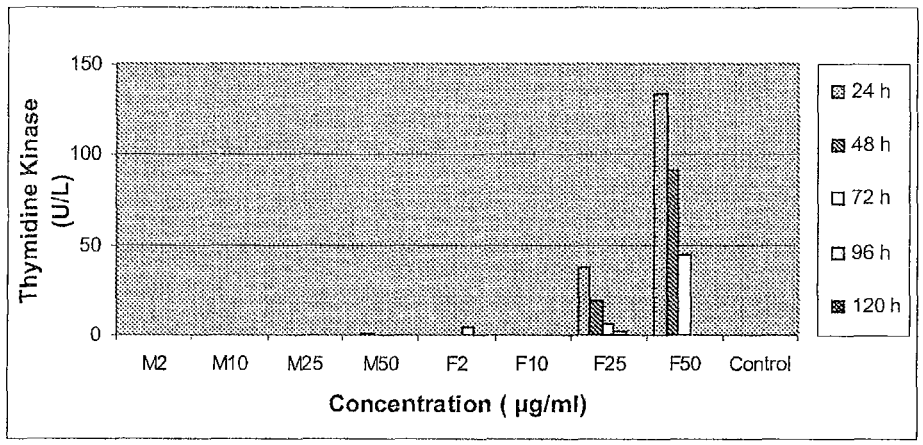

Fig. 9.6
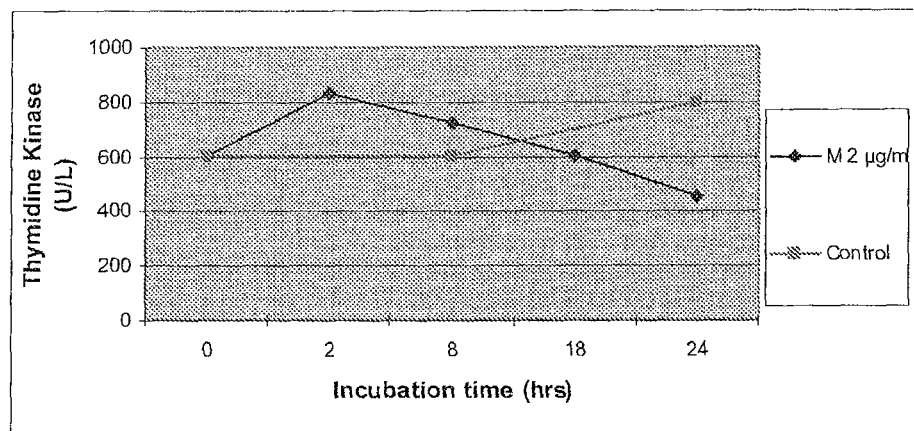
Fig. 9.7
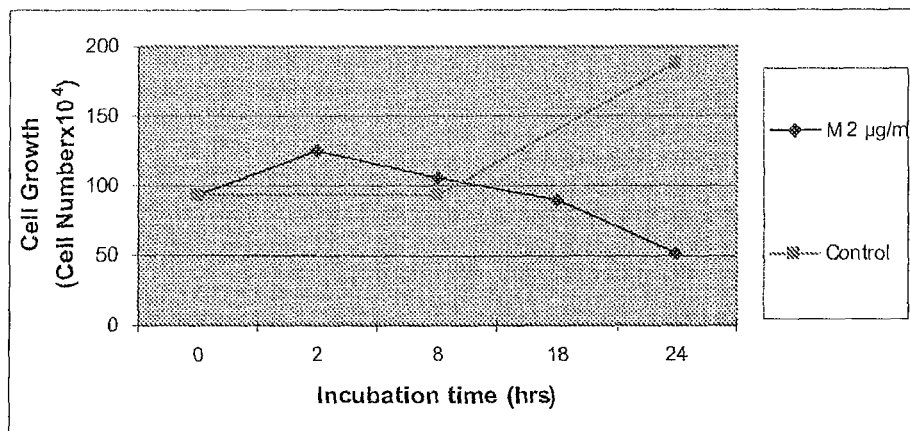
Fig. 9.8
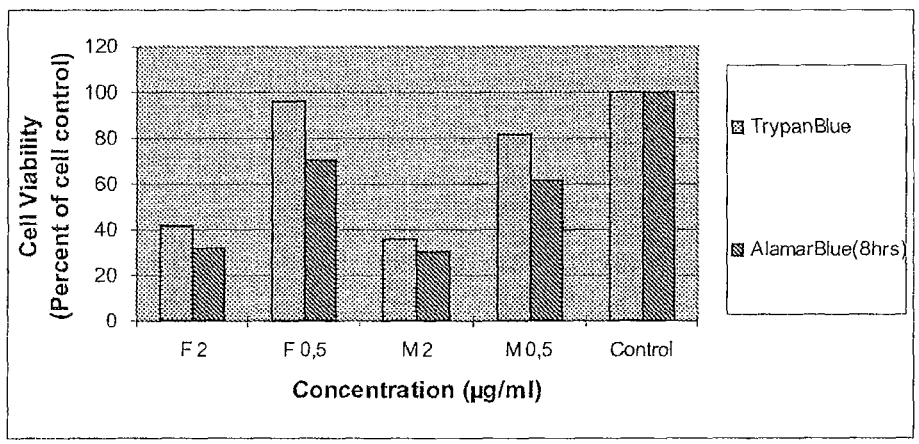

Fig. 10.1.
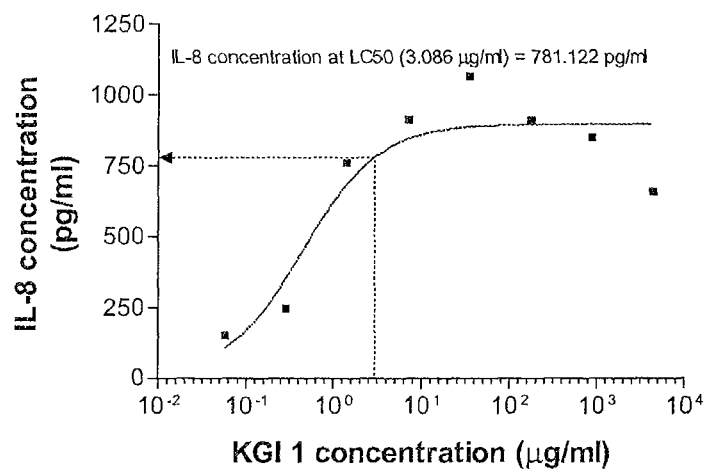
Fig. 10.2
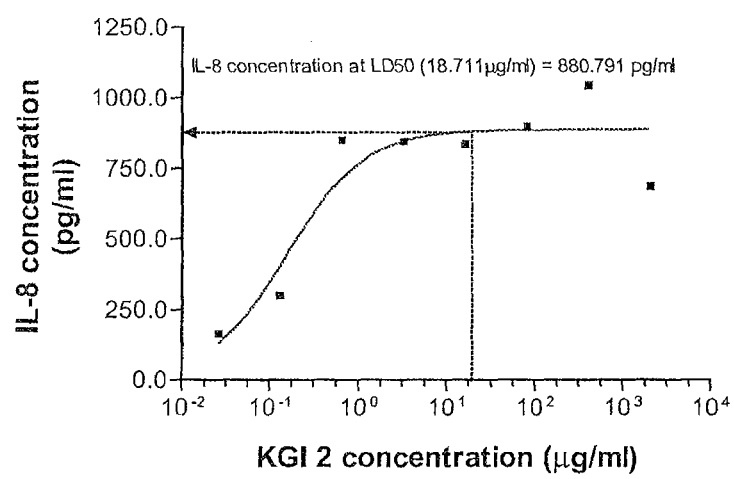

Fig. 10.3
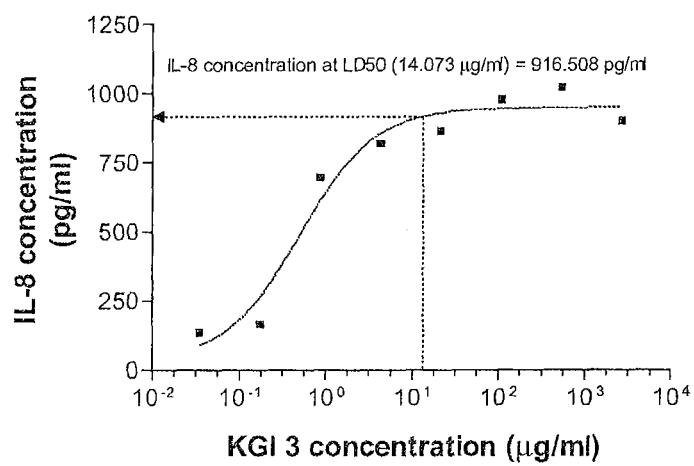

USE OF LIPID CONTAINING PARTICLES COMPRISING QUILLAJA SAPONINS FOR THE TREATMENT OF CANCER

RELATED APPLICATIONS

This application is a U.S. National Stage Filing under 35 U.S.C. 371 from International Application Number PCT/SE2007/050878, filed Nov. 20, 2007 and published in English as WO 2008/063129 A1 on May 29, 2008, which claims the benefit under U.S. Provisional Application Ser. No. 60/866,445, filed Nov. 20, 2006, under 35 U.S.C. 119(e), which applications and publication are incorporated herein by reference in their entirety.

The present invention relates to the use of a lipid containing particle comprising at least one lipid and at least one saponin, such as liposomes, iscom and/or iscom matrix and posintros for the preparation of a pharmaceutical for the treatment of cancer. The particles are also delivery systems for one or several compounds for cancer treatment with complementary mechanisms.

It also relates to a method for the treatment of cancer wherein a lipid containing particle comprising at least on lipid and at least one saponin is administrated to an individual in need of cancer treatment.

Further, the inventions regards kit of parts comprising at least two parts, wherein one part comprises lipid containing particles comprising at least one saponin fraction which is hydrophobic having a killing effect on cancer cells; and the other part comprises lipid containing particles having at least one saponin fraction which is comparatively hydrophilic, stimulating and modulating the immune response such as antibody production and cell mediated immunity.

The present invention relates to the discovery that selected *Quillaja* components in particulate formulations kill and inhibit the growth of tumour cells (hereafter called KGI). The particulate formulations are preferred because they are highly bio-available. They can be formulated with targeting molecules and they can be formulated to be well accepted by man or animal without side effects caused by the lytic effect of the free forms.

THE PRIOR ART

Particles comprising lipids such as liposomes and iscoms have been described as carriers of antigens and adjuvants.

The immune stimulatory properties of *quillaja* saponins have been known for long (Ramon 1926) and *quillaja* saponins have been used in free form, sometimes in combination with $Al(OH)_3$ in commercial vaccines since 1950:s (Dalsgaard 1978), Ma et al. (Ma, Bulger et al. 1994), (Espinet 1951). A substantially more efficient use of the *quillaja* saponins compared to conventional free forms was described by Morein et al. (Morein, Sundquist et al. 1984)—the ISCOM technology (EP 0 109 942 B1, EP 0 242 380 B1 and EP 0 180 564 B1) and a few years later the ISCOM-matrix technology (Lovgren and Morein 1988), (EP 0 436 620 B1). Using the iscom technology vaccine antigens are incorporated into a 40 nm complex consisting of *quillaja* saponins, cholesterol and phospholipid(s).

It is known that *quillaja* saponins present anticancerous activity. However saponins in crude or fractionated forms as such have general side effects because of hydrophobic—lytic effects causing partial trapping at the site of administration. Therefore, free forms of saponins are not realistic in cancer treatment. Consequently saponins as such have not developed into useful cancer drugs.

Further, the iscom technology has been developed into a cancer vaccine comprising cancer antigens integrated into the iscom complex. However, whereas the antigens in these vaccines elicit—an-antibody and cell mediated responses, the iscom complex as such is degraded and will not be present if the individual is affected with cancer cells in the future.

It has now turned out that lipid containing particles comprising at least on lipid and at least one saponin and such as iscoms and iscom matrices may be used for the preparation of a pharmaceutical for the treatment of cancer.

Cancer cells are 30 to 40 times more sensitive than normal cells to the lipid and saponin comprising particles according to the invention. The lipid and saponin containing particles induce apoptosis that kills cancer cells.

The killing effect is due to a prominent apoptosis inducer. High concentration induces earlier apoptosis. After treatment with the lipid containing particles according to the invention the cells do not stay in the cell cycle i.e. they do not exceed to a second cycle. Thus, the killing of cancer cells is irreversible. The production phase is illustrated by the fact that IL-8 production follows by apoptosis.

After a prolonged culture of cancer cells, the cells do not revert to replicate after that the treatment, more significantly, even after exposure to an interrupted low physiological dose.

The cancer cell death has been analysed by several methods including Trypan blue staining, enzymatic metabolic inhibition by the AlamarBlue method, by necrotic changes visualised by propidium iodide staining and by apoptosis via Annexin V staining as described in Materials and Methods.

SUMMARY OF THE INVENTION

The present invention relates to the use of a lipid containing particle comprising at least on lipid and at least one saponin, such as liposomes, iscom and/or iscom matrix and posintros for the preparation of a pharmaceutical for the treatment of cancer.

It also relates to a method for the treatment of cancer wherein a lipid containing particle comprising at least on lipid and at least one saponin is administrated to an individual in need of cancer treatment.

Further, the inventions regards kit of parts comprising at least two parts, wherein one part comprises lipid containing particles comprising at least one saponin fraction which is hydrophobic having a killing effect on cancer cells; and the other part comprises lipid containing particles having at least one saponin fraction which is hydrophilic, stimulating and modulating the immune response such as antibody production and cell mediated immunity.

The present invention relates to the discovery that selected saponins such as *Quillaja* components in particulate lipid containing formulations possess killing and growth inhibiting effects on tumour cells (hereafter called KGI and BBE). The saponin or the saponin fractions are selected for their capacity to kill or inhibit growth of tumour cells. The particulate formulation is selected because of high bioavailability and that the particles can be formulated to be well accepted without side effects by the individuals e.g. man or the animal as compared to free forms of crude saponins or free forms of saponins.

Other saponins or saponin fractions (including fraction QHA from *Quillaja saponaria* Molina) may be selected because they may or may not exhibit such KGI effect, but they exhibit potent neutralizing, blocking and balancing effects on the KGI. These fractions may also in particulate form as part of the KGI particle or in a separate BBE particle kill some cancer cells in synergy with particulate or not particulate QHC. The blocking and balancing effect is, hereafter, contracted to BBE. KGI and BBE particles stimulate and modulate immune protective responses to the tumour antigens either released from cells treated with the KGI particles and killed, which by cross presentation can present antigens, or by the fact that BBE directly can stimulate antigen presenting cells (APCs) to anti-tumour effects.

The invention is further described by the following figures of which:

FIGURE LEGENDS

FIG. 1.1. The triterpenoid structure of *Quillaja* saponin,

FIG. 1.2. The reversed phase profile of *Quillaja* saponin. Fraction C is the main and active component of KGI 1 and fraction A is the main and active component of BBE.

FIG. 1.3. Electron microscopic picture of KGI 1

FIG. 2.1. The structural differences between QHC and QHA. The highly lytic effect of QHC for cell membranes is related to the fatty acyl chain to the right of marked point 3. QHA is lacking the fatty acyl chain rendering it much more hydrophilic and consequently less lytic. Both QHC and QHA are naturally accruing components of non-fractionated *quillaja* saponin (see separation pattern by HPLC in FIG. 1.2).

FIG. 3.1. KGI 1 kills the cancer cell U937 at a low concentration measured by the AlamarBlue method FIG. 3.2. A high dose of KGI 1 is required to kill normal human dendritic cells (DC)

FIG. 4.1. BBE is non-toxic to the U937 tumour cells

FIG. 4.2. BBE is non-toxic to normal human dendritic cells (DC)

FIG. 5.1. In the ratio 10 to 1 between BBE and KGI 1, BBE blocks the killing effect by KGI 1. This test was carried out with a fixed concentration of KGI 1 i.e. 77 µg/ml and increasing concentrations of BBE as shown on the X axis.

FIG. 6.1. KGI 2 has two saponin components (QHA and QHC in various ratios i.e. 9.5:0.5; 7.5:2.5 and 7.0:3.0) in one and the same particle. The cancer killing capacity of KGI 2 on U937 cells increases with increasing proportion of QHC.

FIG. 6.2. KGI 2, having two saponin components (QHA and QHC) in a ratio of 7:3 in one and the same particle, requires a higher concentration of the active substance QHC than KGI 1 (see FIG. 3.1 in example 3) to kill U937 cancer cells FIG. 6.3. KGI 2, having two saponin components (QHA and QHC) in a ratio 7:3 in one and the same particle, requires a higher concentration of active substances QHC than KGI 1 (see FIG. 3.2 in example 3) to kill normal human DCs than to kill U937 cancer cells.

FIG. 6.4. Various KGI and BBE formulations activate monocyte derived immature DCs to mature and express a DC marker CD86 being a molecule of activated DCs communicating to lymphocytes to differentiation and activation to be effector cells.

FIG. 7.1. KGI 1 particles inhibit replication of U937 cancer cells. The cells were seeded in micro titre plates, thereafter were exposed to 2 µg/ml (M2) KGI 1 for the 9 days experimental culture period and the number of viable cells was counted daily by microscopy after staining with the Trypan blue.

FIG. 7.2. KGI 1 particles inhibit replication of U937 cancer cells even after interruption of the exposure to KGI 1. The cells were cultured and exposed for 9 days with 2 µg/ml (M2) to KGI 1 as described in FIG. 7.1. The KGI 1 was removed after 3 days of incubation. At time points indicated by the arrow, the culture medium was replaced. The control cells were cultured without KGI 1.

FIG. 7.3. U937 cancer cells cultured as described in FIG. 7.1., were exposed to the high dose of 25 µg/ml of the free form of KGI 1 i.e. QHC fraction of Quill A (F) or to 25 µg/ml of KGI 1 as particle (M) and sampled as indicated in the Figure. The cells were stained with Trypan blue (see Materials and Methods). Cell viability is expressed as percent of the viable control cells. At this high dose, the free form of KGI 1 i.e. QHC fraction of Quill A killed the cells fast i.e. within 3 hours, while the KGI 1 particle required longer time i.e. 24 hours to kill a high proportion the cancer cells.

FIG. 7.4. U937 cancer cells were exposed to the low physiological dose of 2 µg/ml of the free form of KGI 1 i.e. QHC fraction of Quill A (F) or to 2 µg/ml of KGI 1 (M) as particle as indicated in the Figure. The cells were stained by Trypan blue (see Materials and Methods). Viability is expressed as percent of the viable control cells. At this low dose, the free form of KGI 1 i.e. QHC fraction of Quill A did not kill the cells within 60 hours of culture, while the KGI 1 particle started to kill the cancer cells after 24 hours.

FIG. 7.5. Very low doses of KGI 1 particles inhibit growth of U937 cancer cells. The cells were exposed for 12 days to the low doses of 0.5 µg/ml (M0.5) or to 2 µg/ml (M2) of KGI 1 as indicated in the figure. The number of cells was counted after staining by Trypan blue method (see Materials and Methods). The low dose of 0.5 µg/ml of KGI reduced the cell number compared to the non-treated cells, while the dose of 2 µg/ml of KGI 1 particle killed all cancer cells within the 12 days of culture.

FIG. 7.6. KGI 1 induces apoptosis in U937 cancer cells. The cells were exposed for 120 hours to KGI 1 at the concentrations of 2 µg/ml (M2) or to 25 µg/ml (M25) in the culture medium. The numbers of Annexin V positive cells were determined by FACS (see Materials and Methods). The 2 µg/ml concentration provoked increased population of apoptotic cells with a peak level after 24 hours of exposure. The higher concentration i.e. 25 µg/ml KGI 1 further increased the proportion of apoptotic cells with peak levels after exposure for 12 and 24 hours.

FIG. 7.7. KGI 1 does not provoke an increased number of necrotic U937 cancer cells. The cells were exposed to KGI 1 for a period of 120 hours at concentrations of 2 µg/ml (M2) up to 50 µg/ml (M50) in the culture medium as listed in the figure. The cells were cultured and sampled as described in FIG. 7.1 stained with propidium iodide and the numbers of necrotic cells were determined by FACS (see Materials and Methods). There was no difference in the proportion of necrotic cells between cells treated with various doses of KGI 1 or control cells not exposed to KGI 1.

FIG. 7.8. KGI 1 provokes over time U937 cancer cells to be stained by both Annexin V (apoptosis) and propidium iodide (necrosis). The cells were grown as described in FIG. 7.1 and exposed for 120 hours to KGI 1 at the concentrations from 2 µg/ml (M2) up to 50 µg/ml (M50) in the culture medium. The cells were sampled and stained with propidium iodide and Annexin V as indicated in the figure. The proportions of affected cells were determined by FACS. Increasing concentrations induced an increased population of cells stained for both necrotic and apoptotic effects.

FIG. 8.1. KGI 1 inhibits proliferation of the cancer cell U937 and the cells do not revert to proliferation when followed during a culture period of 12 days. The cells were exposed to 0.5 µg/ml (M0.5) and 2 µg/ml (M2) of KGI 1 in the culture up to 12 days and the samples were collected as indicated in the figure. A turning point towards reduced cell growth is seen after exposure of the cells to KGI 1 for 1 to 3 days. The viable cells were counted after staining with Trypan blue.

FIG. 8.2. KGI 1 inhibits proliferation of the cancer cell U937 and the cells do not revert to proliferation after removal of KGI 1. The cells were first starved for 22 hours to synchronize the cells in the cell cycle (see text). Thereafter, the cells were exposed to 2 µg/ml of KGI 1 in the culture up to 12 days and samples were collected and medium changed every 3:rd day. KGI 1 was removed from the cells on day 3. The viable cells were counted after staining with Trypan blue.

FIG. 9.1. Illustration of the cell cycle. The Thymidin kinase (TK) activity precedes the S-phase i.e. the DNA replication phase. The inhibitory effect of KGI 1 on cell growth seems to take place late in the cell growth cycle at least in low doses.

FIG. 9.2. The TK activity was measured in cell lysate daily after treatment of $10^6$/ml of 0937 cancer cells with 2 µg/ml (M2) or 25 µg/ml (M25) of KGI 1 for 5 days. Cell culture medium was not changed during this experimental period explaining the decrease of activity of the non-treated cells. Reduction of TK activity of treated cells was compared to that of non-treated controls during the 5 days of culture. Reduction of the TK activity after the high dose of 25 µg/ml of KGI 1 is prominent after exposure for 24 hours and for the low dose of 2 µg/ml of KGI 1 after two days.

FIG. 9.3. The TK activity was measured in cell lysate after treatment of $10^6$/ml of U937 cancer cells with 2 µg/ml (M2) or 25 µg/ml (M25) of KGI 1 over a period of 5 days. The TK activity is expressed as percentage of that of non-treated cells (see also FIG. 9.2).

FIG. 9.4. The TK activity was measured in cell lysate daily for 120 hours after treatment of $10^6$/ml of U937 cancer cells with particulate KGI 1 in concentrations of 2 µg/ml (M2), 10 µg/ml (M10), 25 µg/ml (M25) 50 µg/ml (M50). Reduction of TK activity after treatment with particulate KGI 1 was compared to that of free i.e. non-particulate KGI 1 tested in the same concentrations designated with F. At low physiological doses the reduction became prominent after exposure of the cells for 48 hours (M2), but less prominent for free KGI 1 (F2). Reduction of the TK activity after treatment with the high dose of 25 µg/ml or higher concentration of KGI 1 is prominent after exposure for 24 hours. Cells treated with the high doses of free KGI i.e. 25 µg/ml and 50 µg/ml cell culture fluid did not show detectable TK activity (see also FIG. 9.5).

FIG. 9.5. The TK activity was measured in cell culture medium daily after treatment of $10^6$/ml of U937 cancer cells with particulate KGI 1 in concentrations of 2 µg/ml (M2), 10 µg/ml (M10), 25 µg/ml (M25) 50 µg/ml (M50) for 5 days. TK activity was not detected in medium from cells treated with particulate KGI 1. The cells treated with the free i.e. non-particulate KGI 1 tested in the concentrations of 25 µg/ml and 50 µg/ml designated with F, released TK to the culture fluid (see also FIG. 9.4). The exclusive TK activity in cell culture medium, but not in cells, indicates leakage and cell membrane damage.

FIG. 9.6. The Thymidin kinase (TK) activity was analysed in the U937 cancer cells after cell starvation for 22 hours (see text) to synchronize the cells in the cell cycle. Thereafter, the cells were exposed to 2 µg/ml of KGI 1 for 0, 2, 8, 18 and 24 hours. The non-treated controls were sampled at 0, 8 and 24 hours (see text). KGI 1 (2 µg/ml i.e. M2) reduces Thymidine kinase activity of U937 cancer cells recorded in cell samples treated for 18 and 24 hours. The results indicate that no inhibition of TK activity took place with the low dose during the first 8 hours, but after 18 hours.

FIG. 9.7. KGI 1 (2 µg/ml) inhibits proliferation of the cancer cell U937 detected after 18 hours of exposure. First, the cells were starved for 22 hours to synchronize the cell in the cycle (see text). The reduced cell growth after 18 hours of treatment coincides with the reduced TK activity as shown in FIG. 9.6. The viable cells were counted after staining with Trypan blue.

FIG. 9.8. The cell metabolic inhibition (Alamar Blue) and cell killing (Trypan blue) were measured after cell starvation for 22 hours (see text) to synchronize the cells in the cell cycle. Thereafter, the cells were exposed to 2 µg/ml or 0.5 µg/ml of KGI 1 for 24 hours. The non-treated controls were sampled at 24 hours. KGI 1 (2 µg/ml i.e. M2) and free KGI (2 µg/ml i.e. F2) reduced the cell viability after treatment for 24 hours. The concentration of 0.5 µg/ml of KGI 1 or free KGI 1 reduced the cell viability after a treatment period of 24 hour. The metabolic inhibition was more prominent after treatment with KGI 1 than after that with the free form.

FIG. 10.1. KGI 1 induces the cancer cell U937 at a LC50 concentration of 3 µg/ml to produce 781 µg/ml of IL-8.

FIG. 10.2. KGI 2 induces the cancer cell U937 at a LC50 concentration of 19 µg/ml to produce 880 µg/ml of IL-8.

FIG. 10.3. KGI 3 induces the cancer cell U937 at a concentration of 14 µg/ml to produce 917 µg/ml of IL-8.

DETAILED DESCRIPTION OF THE INVENTION

The invention relates to the use of lipid containing particles comprising at least one lipid and at least one saponin for the preparation of a pharmaceutical for the treatment of cancer. Thus, the invention relates to a medicament comprising at least one lipid and at least one saponin for the treatment of cancer.

According to the invention it is the lipid particle as such and the saponin that give the cancer killing effect. It has turned out that even though free saponins as such may kill cancer cells, they also have a negative effect on normal cells. Together with the lipids or integrated into the lipid particles the effect against cancer cells is obtained at a concentration that is 30 times lower than the concentration of the free saponins that is toxic for normal cells.

The lipid containing particles may be chosen from liposomes, iscom and/or iscom matrix and posintros.

Liposomes

A liposome is generally spherical or spheroidal cluster or aggregate of amphipathic compounds, including lipophilic moieties, typically in the form of one or more concentric layers, for example, monolayers, bilayer or multi-layers. They may also be referred to herein as lipid vesicles. The liposomes may be formulated, for example, from ionic lipids and/or non-ionic lipids. Liposomes formulated from non-ionic lipids may be referred to as niosomes. Liposomes formulated, at least in part, from cationic lipids or anionic lipids may be referred to as cochleates.

The liposomes may be prepared e.g. as described by Lipford and Wagner (Lipford, Wagner et al. 1994) and in Gregoriadis, G. (Gregoriadis, McCormack et al. 1999), O'Hagan, D T (2001).

General liposomal preparatory techniques which may be adapted for use in the preparation of liposome compositions pertaining to the present invention are discussed, for example, in U.S. Pat. Nos. 4,728,578, 4,728,575, 4,737,323, 4,533,254, 4,162,282, 4,310,505, and 4,921,706; U. K. Patent Application GB 2193095A; International Application Serial Nos. PCT/US85/01161 and PCT/US89/05040; Mayer et al. (Mayer, Hope et al. 1986); (Hope et al. 1985); Mayhew et al. (Mayhew, Conroy et al. 1987); Mayhew et al. (Mayhew, Lazo at al. 1984); Cheng at al, (Cheng, Seltzer et al. 1987); and Liposome Technology, Gregoriadis, G. (Gregoriadis, G., ed, 1984), the disclosures of each of which are hereby incorporated by reference herein. Accordingly, the liposome compositions may be prepared using any one of a variety of conventional liposomal preparatory techniques which will be apparent to one skilled in the art, including, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the compositions in various fashions. See, e.g., Madden et al., (Madden, Harrigan et al. 1990), the disclosure of which is hereby incorporated herein by reference.

Suitable freeze-thaw techniques are described, for example, in WO application no. PCT/US89/05040, filed Nov. 8, 1989, the disclosure of which is hereby incorporated herein by reference in its entirety. Methods, which involve freeze-thaw techniques, are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing, which may be achieved, for example, by the use of a mechanical shaking device, such as a Wig-L-Bug™ (Crescent Dental, Lyons, Ill.), a Mixomat (Degussa AG Frankfurt, Germany), a Capmix (Espe Fabrik Pharmazeutischer Praeparate GMBH & Co., Seefeld, Oberay Germany), a Silamat Plus (Vivadent, Lechtenstein), or a Vibros (Quayle Dental, Sussex, England). Conventional microemulsification equipment, such as a Microfluidizer™ (Microfluidics, Woburn, Mass.) may also be used.

Iscom and Iscom Matrices

Iscoms comprise at least one saponin such as at least one glycoside, at least one lipid and at least one type of antigen substance. The lipid is at least a sterol such as cholesterol and optionally also phosphatidyl choline. This complexes may also contain one or more other immunomodulatory (adjuvant-active) substances, and may be produced as described in EP 0 109 942 B1, EP 0 242 380 B1 and EP 0 180 564 B1.

The iscom matrix complex in the compositions of the invention comprises at least one glycoside and at least one lipid. The lipid is at least a sterol such as cholesterol and optionally also phosphatidyl choline. Matrix has an immunoenhancing effect on co-administered antigenic substances. The iscom complexes may also contain one or more other immunomodulatory (adjuvant-active) substances, not necessarily a saponin, and may be produced as described in EP 0 436 620 B1 and may be produced as described in this patent.

One or more iscom particles, one or more iscom matrix particles or any sub-fragment(s) of the 6 nanometer rings thereof may be used. Any mixtures of such iscom matrix, particles or sub fragments may be used.

Posintros

Posintros are complexes comprising: i) at least one first sterol and/or at least one second sterol, wherein the at least one second sterol is capable of contacting a foreign antigen, preferably a nucleic acid by means of an interaction selected from an electrostatic interaction and a hydrophobic interaction, and wherein the at least one first sterol and/or the at least one second sterol is capable of forming a complex with at least one first saponin and/or at least one second saponin, and ii) at least one first saponin and/or at least one second saponin, wherein the at least one second saponin is capable of contacting a genetic determinant by means of an interaction selected from an electrostatic interaction and a hydrophobic interaction, and wherein the at least one first saponin and/or the at least one second saponin is capable of forming a complex with at least one first sterol and/or at least one second sterol, and optionally iii) at least one contacting group for contacting a genetic determinant by means of an interaction selected from an electrostatic interaction and a hydrophobic interaction, with the proviso that the at least one contacting group is present when no second sterol is present in the complex and further optionally i) at least one lipophilic moiety.

Posintros may adopt a micro-particle structure in the form of a cage-like matrix similar to that known as an immune stimulating complex (iscom). Beside iscom structures, the interaction between sterols and saponins have been reported to result in a variety of different structural entities, including entities such as e.g. lattices, honeycombs, rods, and amorphic particles, all of which structural entities are covered by the present invention.

Posintros are described in WO patent applications no WO 2002/080981 and WO 2004/030696.

Lipids

The lipids used are particularly those described in the applicant's patent EP 0 109 942 B1 in particular on p. 3 and in patent EP 0 436 620 B1 on p. 7 lines 7-24. Especially sterols such as cholesterol and phospholipids such as phosphatidylethanolamin and phosphatidylcolin are used. Lipid-containing receptors that bind to the cell-binding components, such as glycolipids including the cholera toxin's receptor, which is the ganglioside GM1, and fucosed blood group antigen may be used. The cell-binding components can then function as mucus targeting molecule and be bound to the lipid-containing substances through simply mixing them with complexes that contain them. Iscom complexes comprising such receptors and receptors are described in WO 97/30728

Saponins

The saponins may be any saponin. According to one aspect of the invention the saponins are glycosides obtained from plants. The plant glycoside may be chosen from sapogeins and prosapogenins with one or more sugar moieties. The glycoside may be a crude saponin fraction from *Quillaja saponaria* Molina or a sub fraction thereof.

*Quillaja* saponin and various fractions thereof have been used as adjuvant and in various adjuvant formulations since the $50^{th}$ and among the most hydrophobic fractions, e.g. QS21, has been used in animal vaccines and in various human clinical tests (Kersten, Spiekstra et al. 1991); (Kensil, Patel et al. 1991). ISCOM or the ISCOM MATRIX have been formed with various *quillaja* fractions or with various combinations of fractions or more crude *Quillaja* saponin. In all instances the ISCOM or ISCOM MATRIX formulations have caused less local reactions than the free forms. Recent developments have designed formulations that have superior immune enhancing capacity and are much more tolerated than any other *Quillaja* saponin formulation used as adjuvant (Morein, Sundquist et al. 1984). Components of these well-tolerated *Quillaja* saponin formulations are used in the present invention for cancer cell killing (KGI) and for balancing the effects (BBE).

Saponins are molecular complexes consisting of an aglycone to which one or more sugar chains are attached. The saponin may be acylated with organic acids such as acetic, malonic as apart of their structure (Hostettmann K, and Marston A. 1995; Rouhi A. M. 1995; Leung A Y., and Foster S. 1996). These complexes have MW ranging from 600 and to more than 2000 kd. The hydrophobic aglycan and the hydrophilic sugar moiety render an amphipathic property. In particular triterpene glycosides are of interest. Other saponins characterized by their aglycone are steroid glycosides and steroid alkaloid glycosides.

Crude *Quillaja* saponin was first isolated in 1887 by Kobert, R., Arch. Exp. Pathol. Pharmakol. 23: 233-272, 1887.) Later Dalsgaard purified *Quillaja* saponin (Dalsgaard 1974). Higuchi, R. (Higuchi, R. 1988) reported the complete structure of *Quillaja* saponin recognizing an aglucone (triterpenoid quillaic acid) attaching two sugar moieties at two different positions. Useful glycosides are described in EP 0 109 924 B1. Saponins and triterpensaponins are preferred. They may be in the form of raw extract from *Quillaja saponaria* Molina" (Dalsgaard 1974), or any sub fraction thereof as described in PCT/US/88101842 to Kensil et al. (Kensil, Patel et al. 1991), (Kersten, Spiekstra et al. 1991). "Aspects of (scorns. Analytical, Pharmaceutical and Adjuvant Properties; Thesis, University of Utrecht, EP 0 362 279 B2 and EP 0 555 276 B1.

The term "one saponin fraction from *Quillaja saponaria* Molina." is used throughout this specification and in the claims as a generic description of a semi-purified or defined saponin fraction of *Quillaja saponaria* or a substantially pure fraction. It is important that the fraction does not contain as much of any other fraction to negatively affect the good results that are obtained when the mixtures of iscom or iscom matrix comprising essentially one fraction is used. The saponin preparation may, if desired, include minor amounts for example up to 40% by weight, such as up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight up to 0.1% by weight of other compounds such as other saponins or other adjuvant materials.

The saponin fractions according to the invention may be the A, B and C fractions described in WO 96/11711, the B3, B4 and B4b fractions described in EP 0 436 620 The fractions QA1-22 described in EP 0 3632 279 B2, Q-VAC (Nor-Feed, AS Denmark), *Quillaja saponaria* Molina Spikoside (Isconova AB, Ultunaallén 2B, 756 51 Uppsala, Sweden)

The fractions QA-1-2-3-4-5-6-7-8-9-10-11-12-13-14-15-16-17-18-19-20-21 and 22 of EP 0 3632 279 B2, Especially QA-7, 17-18 and 21 may also be used. They are obtained as described in EP 0 3632 279 B2, especially at page 6 and in Example 1 on page 8 and 9. Fractions A, B and C described in WO 96/11711 are prepared from the lipophilic fraction obtained on chromatographic separation of the crude aqueous *Quillaja saponaria* Molina extract and elution with 70% acetonitrile in water to recover the lipophilic fraction. This lipophilic fraction is then separated by semi preparative HPLC with elution using a gradient of from 25% to 60% acetonitrile in acidic water. The fraction referred to herein as "Fraction A" or "QH-A" is, or corresponds to, the fraction, which is eluted at approximately 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is elated at approximately 49% acetonitrile.

Saponins from *Quillaja saponaria* Molina can be divided into two different categories that is;
(I) The more hydrophobic fractions have a fatty acid acyl chain at position 4. These saponin fractions exhibit strong lytic effect by making small, around 12 nm holes in cell membranes. Such saponin fractions kill irreversibly cells in free forms, but not necessarily in the particulate form of immuno-stimulating complexes with integrated antigens (ISCOM) or the similar particle without an integrated antigen i.e. ISCOM MATRIX in moderate concentrations (Ronnberg, Fekadu et al. 1997) and as described in the present invention.
(II). The more hydrophilic *Quillaja* saponins can be given in ten fold higher concentrations or more before exhibiting cell lytic effects. In particulate form these saponin fractions have virtually no cell toxic effect or virtually no toxic effect in vivo.

The particulate forms of the more hydrophobic and the more hydrophilic forms are described as ISCOM MATRIX, which are 40 nm spheres built up by 6 nm ring formed sub-fragments (Ronnberg, Fekadu et al. 1995), (Lovgren and Morein 1991).

The lipid particles such as iscom and iscom matrix comprising hydrophobic saponins e.g. to comprising fatty acids are in the present invention named KGI particles (killing and growth inhibiting tumour cells). Such saponins may be fractions that do contain fatty acyl e.g. in the 4-position in the triterpenoid aglycone of the saponins from *Quillaja saponaria* Molina such as fraction C and B of Quil A or fractions from the region between fractions A and B and fractions 15-21 described in EP 0 3632 279 B2, especially fractions 16, 17, 18 are suitable here.

The lipid particles such as iscom and iscom matrix composed with saponins with hydrophilic saponins e.g. composed with the fatty acid are named BBE particles (with blocking balancing effect and also cancer cell killing effect). Fractions 4-15 of Quil A, especially 7-14 described in EP 0 3632 279 B2 and fraction A (QHA) are suitable here.

The lipid particle may comprise at least on hydrophobic saponin. It may also comprise at least one hydrophilic saponin. The at least one hydrophilic saponin and the at least one hydrophobic saponin may be in one and the same or in different lipid containing particles.

The QHA fraction from *Quillaja saponaria* Molina selected because it does not exhibit cell killing effect, but it exhibits potent neutralizing, blocking or more importantly a balancing effects on the KGI formulations e.g. a balance between killing of cells and modulation towards differentiation. The blocking and balancing effect is, hereafter, contracted to BBE. KGI and BBE particles stimulate and modulate immune protective responses to antigens. It is anticipated that these particles may, therefore, stimulate immune responses to the tumour antigens released from cells killed by the KGI particles, which by cross presentation can present antigens. Alternatively, BBE can directly enhance stimulation of antigen presenting cells (APCs) to anti-tumour effects as well as the induction of an acquired anti-tumour immune response.

Thus, the KGI and the BBE particles, as named for their functions in this invention, have different properties KGI can irreversibly block cell growth and kill cancer cells at comparatively low concentrations i.e. at 30 to 40 times lower concentration than those for primary human or murine cells. Besides, KGI like BBE have (has) an immune enhancing effect on incorporated antigens or antigens in its environment released from cells or co-administered. BBE particles may be co-administered with KGI particles with tumour antigen integrated or get tumour antigens spontaneously from cancer cells e.g. destroyed by KGI or co-administered antigenic substances, see EP 0 436 620 B1.

Both KGI and the BBE comprise at least one saponin such as a glycoside and at least one lipid If they are iscoms and iscom matrixes they also comprises the lipid cholesterol as described in WO/1990/003184.

The lipid containing particles comprising hydrophobic saponins that have a killing effect on cancer cells may also further comprise hydrophilic saponins.

The lipid containing particles may contain at least two different saponin fractions in one and the same lipid containing particle.

The lipid containing particles may also contain at least two different saponin fractions, whereby one of the at least two different saponin fractions is complex bound in one lipid containing particle and the other one (the other ones) of the at least two different saponin fractions is (are) complex bound in another (other) physical different lipid containing particle(s).

The different saponins may be hydrophilic and hydrophobic saponins respectively. The particle may contain at least fraction C or at least fraction B or at least any fraction between fraction C and B of Quil A and at least one other fraction of Quil A. Thus one particle may comprise fraction C only; fraction C and at least one other fraction of Quil A; fraction C and one or more fractions of Quil A; fraction C and fraction A of Quil A; crude Quil A. The particle may also contain fraction B only; fraction B and at least one other fraction of Quil A; fraction B and one or more fractions of Quil A; fraction B and fraction A of Quil A. The above combinations of fractions may also be in different lipid particle or in one and the same lipid particle. The KGI 1, KGI 2 and KGI 3 particles of Example 1 are examples of such lipid particles.

According to one aspect of the invention the KGI particle may comprise crude or raw extract of Quil A comprising a mixture of saponins or a semipurified form thereof such as *Quillaja* Powder Extract (Berghausen, USA), *Quillaja* Ultra Powder QP UF 300, *Quillaja* Ultra Powder QP UF 1000 or Vax-Sap (all three from Natural Responses, Chile). The purified saponin fractions C and B solitary or combined together with A are used in KGI particles while A is used in BBE particles according to the invention. The B and C fractions are described in WO 96/11711, the B3, B4 and B4b fractions described in EP 0 436 620. The fractions QA1-22 described in EP 0 3632 279 B2, Q-VAC (Nor-Feed, AS Denmark), *Quillaja saponaria* Molina Spikoside (Isconova AB, Uppsala Science Park, 751 83, Uppsala, Sweden). Such KGI particles are denoted KGI 3 the examples.

Examples of useful saponins in the KGI particles are the QHC fraction of Quil A and different combinations of the QHC and QHA fractions of Quil A mentioned above. In the examples the KGI 1 particles contain fraction QHC only. The KGI 2 particles contain 30% of QHC and 70% of QHA. All the other combinations of Quil A (*quillaja* saponin) fractions mentioned above may also be used.

Tumour cells are rapidly growing undifferentiated cells. Tumour cells are, therefore, (also) sensitive to certain cell toxic substances. The concept according to the invention is to use substances in particulate form (working name KGI 1, KGI 2 and KGI 3 and BBE) based on fractions or combinations of fractions of *Quillaja saponaria* Molina that having toxic and/or modulator effect on (for) rapidly growing cells like those in malign cancers not excluding benign cancers. The toxic or modulatory effect can be measured on cellular level. The cell toxic—cell modulator substance i.e. the saponin is built into one or more delivery particles. Another particle can besides the toxic or cell modulatory effect also be used to block the toxicity (working name BBE). I.e. a balanced killing system for tumour cells can be created. In the delivery system an immune modulator can be incorporated that stimulate the survival and activate the cells to differentiation. The further stimulation may include induction of cytotoxic T cells being the major immune defense cell type for elimination of cancer. Dying cells of the lymphatic system may also contribute to the stimulation of viable DCs by so-called cross-presentation. Here a monocytes derived monoblastoid cell represents the lymphoma tumour cell and the normal cell is of monocyte origin derived dendritic cell.

By combining KGI and BBE complexes prepared from *quillaja saponaria* Molina it is possible to prepare preparations having different and complementary properties such as lower cell toxicity than KGI particles, complementary cell activation and differentiation and prominent immune-modulatory effect. The effects of KGI and BBE particles are receptor mediated as emphasized by the blocking effect by BBE on KGI to cause cancer cell cytotoxicity. Thus, the cancer cell killing effect of KGI on the U937 cells used as model in this invention is not identified on BBE particles. However, BBE exhibits killing effect on some other cancer cells. The common receptor exerts activation and differentiation of cancer cells, which on normal cells is compatible with or partly compatible with adjuvant activity resulting in cytokine production and expression of e.g. communication molecules e.g. CD 86. CD 86 communicates dendritic cells (DCs) with lymphocyte populations resulting in antigen specific responses, lack of which in e.g. new-borns or elderly hampers the immune response. To note, it has been discovered by the inventors that the fraction QHA (component in BBE and KGI 2) and QHC (component in KGI 1 and KGI 2) activate and differentiate the immune response of newborns harbouring innate and acquired undeveloped or incompletely differentiated immune systems (Hu et al. 2004, Morein & Hu 2007). The receptor provoking cancer cell killing through apoptosis is present on KGI particles but not observed on BBE particles. However, it cannot be excluded that BBE provokes apoptosis on other cancer cells. It cannot be excluded that a cancer cell killing receptor by its own or in conjunction with a second receptor may cause side effects. Particularly, it has to be considered that there are species differences that make a receptor activity or a combination of receptor activities to cause side effects. A system with capacity to deal with such problems is desired and the combination of KGI and BBE gives that possibility.

Thus, KGI killing of cells is receptor mediated since this effect can be blocked by BBE. The common (blocking) receptor for KGI and BBE is thought to be different from that of the receptor mediating killing og U937 cells by KGI 1 containing saponin fraction QHC only. Otherwise BBE should also be an U937 cancer cell killer used in these experiments. The active substance in BBE is QHA. When that is present in the same particle as QHC designated KGI 2 it moderates the cell(s) killing effect by dilution of "killing receptors in QHC", alternatively modifying the structure, resulting in less affinity between ligands and receptors active in cell killing. In contrast, in different particles there is a blocking by the common receptor.

The use of saponin preparations according to this invention results in products with increased tolerability, increased bioavailability immunogenicity. The preparations may be used in methods to tailor the immunogenicity including increased control of inflammatory, hypersensitivity and allergic reactions. This tailor making may be species dependent and may affect toxicity, tolerability and immunogenicity.

It has turned out that when mixtures of lipid containing particles comprising at least one hydrophilic saponin, e.g. fraction A from Quil A (e.g. a BBE particle) is used together with lipid containing particles comprising at least one hydrophobic saponin e.g. fraction C from Quil A (e.g. KGI 1, KGI 2 and KGI 3) a synergistic anticancer effect is obtained.

The at least one hydrophilic saponin may be one or more of fractions 4, 5, 6, 7, 8, 9, 10, 11, 12, 13, 14 and 15 of Quil A, especially fractions 7, 8, 9, 10, 11, 12, 13 and 14 described in EP 0 3632 279 B2 and fraction A of Quil A or crude Quil A.

The at least one hydrophobic saponin may be one or more of saponins that do contain fatty acyl chain e.g. in the 4-position in the triterpenoid aglycone of the saponins from *Quillaja saponaria* Molina such as fraction C and B of Quil A or fractions from the region between fractions A and B and fractions 15, 16, 17, 18, 19, 10 and 21 described in EP 0 3632 279 B2, especially fractions 17 and 18 are suitable here.

The lipid containing particles for such symbiotic effect may be chosen from iscom and iscom matrix particles, liposomes and posintros.

Any ratio of hydrophilic and hydrophobic saponins such as sub fragments of *Quillaja saponaria* Molina saponins may be used. Also, any combination of different hydrophilic and hydrophobic saponins sub fragments of *Quillaja saponaria* Molina may be used. Thus, one, two or more hydrophilic and hydrophobic saponins such as sub fragments *Quillaja saponaria* Molina saponins may each be integrated into physically one and the same or physically separate lipid containing particles.

Any combinations of weight % of the different lipid containing particles such as iscom, iscom matrix complexes, liposomes or posintros based on their content of hydrophilic saponin e.g. fraction A and hydrophobic saponin e.g. C of *Quillaja saponaria* Molina respectively may be used. The mixtures may comprise from, 0.1 to 99.9 by weight, 5 to 95% by weight, 10 to 90% by weight 15 to 85% by weight, 20 to 80% by weight, 25 to 75% by weight, 30 to 70% by weight, 35 to 65% by weight, 40 to 60% by weight, 45 to 55% by weight, 40 to 60%, by weight, 50 to 50% by weight, 55 to 45% by weight, 60 to 40% by weight, 65 to 35% by weight, 70 to 30% by weight, 75 to 25% by weight, 80 to 20% by weight, 85 to 15% by weight, 90 to 10% by weight, 95 to 05% by weight, of lipid containing particles e.g. iscom complexes comprising hydrophilic saponin e.g. fraction A of *Quillaja saponaria* Molina and the rest up to 100% in each case of interval of lipid containing particles e.g. iscom complexes comprising hydrophobic saponin e.g. fraction C of *Quillaja saponaria* Molina, counted on the content of the sum hydrophilic and hydrophobic saponins e.g. fractions A and C of *Quillaja saponaria* Molina in the iscom complexes. This applies for lipid containing particles comprising both hydrophilic and hydrophobic saponins or mixtures of lipid containing particles comprising hydrophobic or hydrophilic saponins only.

Thus, a lipid containing particle may comprise from 75% to 99.5% by weight of hydrophilic saponin e.g. fraction A of Quil A and 0.5% to 25% by weight of hydrophobic saponin e.g. fraction C of Quil A; 80%-95% of hydrophilic saponin and 5-20% of hydrophobic saponin; 85%-90% of hydrophilic saponin and 10-15% of hydrophobic saponin such as 75%, 76%, 77%, 78%, 79%, 80%, 81%, 82%, 83%, 84%, 85%, 96%, 87%, 88%, 89%, 90%, 91%, 92%, 93%, 94%, 95%, 96%, 97%, 98%, 99%, 99.5% by weight of hydrophilic saponin e.g. fraction A and 0.5% 1%. 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% by weight of hydrophobic saponin e.g. fraction C.

All intervals mentioned above may be used for any combination of any fraction of *Quillaja saponaria* Molina in formulations for administration to any type of human or animal species. Examples of animal species to which the formulations according to the invention may be administered are companion animals such as cats, dogs, horses, birds such as parrots, economical important species such as cattle, e.g. bovine species, swines, sheep, goats. Preferably more than 50% by weight of fraction C is used in combination with any of the other fractions and especially in combination with fraction A. Thus, from 50.5-99.5% by weight of C and 0.5-49.5% by weight of A may be used.

When prepared as described herein, Fractions A, B and C of *Quillaja saponaria* Molina each represent groups or families of chemically closely related molecules with definable properties. The chromatographic conditions under which they are obtained are such that the batch-to-batch reproducibility in terms of elution profile and biological activity is highly consistent.

Antigens in the Lipid Containing Particles

The lipid containing particles (such as liposomes, posintros, iscom, iscom matrix, BBE and/or KGI) may comprise cancer antigens integrated into the particles, coupled on to the particles or mixed with the lipid containing particles. These cancer antigens may be used for provoking anticancer immunity.

The tumour antigen(s) may be of the kind as the tumour under treatment, or the lipid containing particle e.g. the KGI may cause release of tumour antigens after killing the tumour cell and cause or enhance initiation of anti-tumour immune response by the cross presentation to bystander antigen presenting cells (APCs). BBE may also contain selected tumour antigen(s) and initiate immune response to integrated, co-administered or spontaneously occurring tumour antigens e.g. released by KGI particles killing tumour cells.

Both lipid containing particles that contain antigens e.g. iscoms and lipid containing particles that do not contain antigens e.g. iscom matrices may be used according to the invention. Lipid containing particles that also comprise antigens such as iscoms are primarily intended for activity against established cancer cells. The lipid containing particles such as iscom matrices that do contain antigens may according to one embodiment contain at least one cancer antigen. According to another embodiment they do not contain cancer antigens.

The immunogen which is incorporated into iscoms may also be associated with the iscom matrix and may be any chemical entity which can induce an immune response in an individual such as (but not limited to) a human or other animal, including but not limited to a humoral and/or cell-mediated immune response to bacteria, viruses, mycoplasma or other micro-organisms. The specific immunogen can be a protein or peptide, a carbohydrate, polysaccharide, a lipopolysaccharide or a lipopeptide; or it can be a combination of any of these.

Particularly, the specific immunogen can include a native protein or protein fragment, or a synthetic protein or protein fragment or peptide; it can include glycoprotein, glycopeptide, lipoprotein, lipopeptide, nucleoprotein, nucleopeptide; it can include a peptide-peptide conjugate; it can include a recombinant nucleic acid expression product.

Examples of such immunogens are cited in EP 0 109 942 B1 and include, but are not limited to, those that are capable of eliciting an immune response against viral or bacterial hepatitis, influenza, diphtheria, tetanus, pertussis, measles, mumps, rubella, polio, pneumococcus, herpes, respiratory syncytial virus, haemophilias influenza, chlamydia, vari-cella-zoster virus, rabies or human immunodeficiency virus.

The antigens may be incorporated into iscom or coupled on to iscom or iscom matrix or mixed with iscom and/or iscom matrix. Any mixtures of such iscom or iscom matrix may be used. One or more antigens may be used and a transport and passenger antigen may be used as described in EP 9600647-3 (PCT/SE97/00289).

Adjuvants.

The lipid containing particles may be used as delivery systems for other components. One type of such components that may be delivered in the lipid containing particles or mixed therewith is adjuvant. Thus, further adjuvants other than saponins may be integrated into the lipid containing particles, coupled on to the particles or mixed with them. Adjuvant effects considered in cancer therapy and under development as therapeutic agents e.g. phorbol esters, vitamin A2 and vitamin D3.

The particles of this invention may contain other immunostimulating and enhancing components than saponins e.g. lipopolysaccharides (LPS), Lipid A, CTB, CTA or CTA1-DD. BBE and KGI may also contain other cancer cell killing agents or cell toxic substances such as cholera toxin (CT) or fractions thereof, heat labile E. coli toxin (LT) or sub fractions thereof.

Moreover, all types of saponines mentioned above may be used as such further adjuvants.

The solutions or suspensions could also comprise at least one of the following adjuvants: sterile diluents such as water for injection, saline, fixed oils, polyethylene glycols, glycerol, propylene glycol or other synthetic solvents, antibacterial agents such as benzyl alcohol or methyl paraben, antioxidants such as ascorbic acid or sodium bisulfite, chelating agents such as ethylene diamine tetraacetic acid, buffers such as acetates, citrates or phosphates, and agents for adjustment of the tonicity such as sodium chloride or dextrose. The parenteral preparation could be enclosed in ampoules, disposable syringes or multiple dosage vessels made of glass or plastic.

Examples of other adjuvants that can be incorporated in the iscom and iscom matrix are any adjuvant, natural or synthetic, with desired immunomodulatory effect, e.g. muramyl dipeptide (MDP)-derivatives, such as fatty acid, substituted MDP, threonyl analogues of MDP; DDA, poly anions such as Dextran sulphate, lipopolysaccharides such as saponins (other than Quil A). Future prospects for vaccine adjuvants (Warren and Chedid 1988); "Characterisation of a non-toxic monophosphoryl lipid A" (Johnson, Tomai et al. 1987); "Developmental status of synthetic immunomodulators" (Berendt and Ives 1985); "Immunopotentiating conjugates", (Stewart-Tull 1985), (Morein et al. 2007).

Anti-Cancer Agents

The lipid containing particles may also be used as delivery systems for anti-cancer agents. They may be delivered in the lipid containing particles or mixed therewith.

KGI and BBE may be used as delivery systems also for other cancer drugs particularly killing by other mechanisms. KGI and BBE contribute with silent killing over activation—differentiation leading to apoptosis. Other therapeutic agents have other cancer cell killing effects. The combinations will certainly contribute to avoiding reversion of cancer cells making them resistant to the treatment.

The further anti-cancer agents are preferably selected from namely platinum coordination compounds, taxane compounds, camptothecin compounds, anti-tumour vinca alkaloids, anti-tumour nucleoside derivatives, nitrogen mustard or nitrosourea alkylating agents, anti-tumour anthracycline derivatives, trastzumab and anti-tumour podophyllotoxin derivatives.

The term "platinum coordination compound" is used herein to denote any tumour cell growth inhibiting platinum coordination compound which provides platinum in the form of an ion. Preferred platinum coordination compounds include cisplatin, carboplatin, chloro (diethylenetriamine)-platinum (II) chloride; dichloro (ethylenediamine)-platinum (II); diamine (1,1-cyclobutanedicarboxylato)-platinum (II) (carboplatin); spiroplatin; iproplatin; diamine (2-ethylmalonato)-platinum (II); (1,2-diaminocyclohexane) malonato-platinum (II); (4-carboxyphthalo) (1,2-diaminocyclohexane) platinum (II); (1,2-diaminocyclohexane)-(isocitrato) platinum (II); (1,2-diaminocyclohexane)-cis-(pyruvato) platinum (II); and (1,2-diaminocyclohexane)-oxalato-platinum (II); ormaplatin and tetraplatin.

Cisplatin is commercially available for example under the trade name Platinol from Bristol Myers Squibb Corporation as a powder for constitution with water, sterile saline or other suitable vehicle. Other platinum coordination compounds and their pharmaceutical compositions are commercially available and/or can be prepared by conventional techniques.

The taxane compound may be those sold under the trade name Taxol from Bristol Myers Squibb and docetaxel is available commercially under the trade name Taxotere from Rhone-Poulenc Rorer. Both compounds and other taxane compounds may be prepared in conventional manner for example as described in EP 253738, EP 253739 and WO 92/09589 or by processes analogous thereto.

Camptothecin compounds include irinotecan and topotecan. Irinotecan is commercially available for example from Rhone-Poulenc Rorer under the trade name Campto and may be prepared for example as described in European patent specification No. 137145 or by processes analogous thereto. Topotecan is commercially available for example from SmithKline Beecham under the trade name Hycamtin and may be prepared for example as described in European patent specification No. 321122 or by processes analogous thereto. Other camptothecin compounds may be prepared in conventional manner for example by processes analogous to those described above for irinotecan and topotecan.

Anti-tumour vinca alkaloids include vinblastine, vincristine and vinorelbine referred to above. Vinblastine is commercially available for example as the sulphate salt for injection from Eli Lilly and Co under the trade name Velban, and may be prepared for example as described in German patent specification No. 2124023 or by processes analogous thereto. Vincristine is commercially available for example as the sulphate salt for injection from Eli Lilly and Co under the trade name Oncovin and may be prepared for example as described in the above German patent specification No. 2124023 or by processes analogous thereto. Vinorelbine is commercially available for example as the tartrate salt for injection from Glaxo Wellcome under the trade name Navelbine and may be prepared for example as described in U.S. Pat. No. 4,307,100, or by processes analogous thereto Other anti-tumour vinca alkaloids may be prepared in conventional manner for example by processes analogous to those described above for vinoblastine, vincristine and vinorelbine.

Anti-tumour nucleoside derivatives include 5-fluorouracil, gemcitabine and capecitabine referred to above. 5-Fluorouracil is widely available commercially, and may be prepared for example as described in U.S. Pat. No. 2,802,005. Gemcitabine is commercially available for example from Eli Lilly under the trade name Gemzar and may be prepared for example as described in European patent specification No. 122707 or by processes analogous thereto.

Capecitabine is commercially available for example from Hoffman-La Roche under the trade name Xeloda and may be prepared for example as described in European patent specification No. 698611 or by processes analogous thereto. Other anti-tumour nucleoside derivatives may be prepared in conventional manner for example by processes analogous to those described above for capecitabine and gemcitabine.

Nitrogen mustard compounds include cyclophosphamide and chlorambucil. Cyclophosphamide is commercially available for example from Bristol-Myers Squibb under the trade name Cytoxan and may be prepared for example as described in U. K. patent specification No. 1235022 or by processes analogous thereto. Chlorambucil is commercially available for example from Glaxo Welcome under the trade name Leukeran and may be prepared for example as described in U.S. patent specification No. 3046301, or by processes analogous thereto. Preferred nitrosourea compounds for use in accordance with the invention include carmustine and lomustine referred to above. Carmustine is commercially available for example from Bristol-Myers Squibb under the trade name BiCNU and may be prepared for example as described in European patent specification No. 902015, or by processes analogous thereto. Lomustine is commercially available for example from Bristol-Myers Squibb under the trade name CeeNU and may be prepared for example as described in U.S. patent specification No. 4377687, or by processes analogous thereto.

Anti-tumour anthracycline derivatives include daunorubicin, doxorubicin and idarubicin referred to above. Daunorubicin is commercially available for example as the hydrochloride salt from Bedford Laboratories under the trade name Cerubidine, and may be prepared for example as described in U.S. patent specification No. 4020270, or by processes analogous thereto.

Doxorubicin is commercially available for example as the hydrochloride salt from Astra, and may be prepared for example as described in U.S. patent specification No. 3803124 or by processes analogous thereto. Idarubicin is commercially available for example as the hydrochloride salt from Pharmacia & Upjohn under the trade name Idamycin, and may be prepared for example as described in U.S. Pat. No. 4,046,878 or by processes analogous thereto Other anti-tumour anthracycline derivatives may be prepared in conventional manner for example by processes analogous to those described above for daunorubicin, doxorubicin and idarubicin.

Trastzumab is commercially available from Genentech under the trade name Herceptin and may be obtained as described in U.S. Pat. No. 5,821,337 or PCT patent specifications WO 94/04679 and WO 92/22653.

Anti-tumour anti-tumour podophyllotoxin derivatives include etoposide and teniposide. Etoposide is commercially available for example from Bristol-Myers Squibb under the trade name VePesid, and may be prepared for example as described in European patent specification No. 111058, or by processes analogous thereto. Teniposide is commercially available for example from Bristol-Myers Squibb under the trade name Vumon and may be prepared for example as described in PCT patent specification No. WO 93/02094, or by processes analogous thereto. Other anti-tumour podophyllotoxin derivatives may be prepared in conventional manner for example by processes analogous to those described above for etoposide and teniposide.

Saponins in crude form or fractions thereof such as those mentioned above may also be used in free form, i.e. not integrated into lipid comprising particles, as anti-cancerous agents. These anticancer compounds may be mixed with, coupled on to or integrated into the lipid containing particles such as liposomes, iscom and/or iscom matrix and posintros.

It is suitable if they are hydrophobic when integrated. If not hydrophobic groups may be coupled on to them as described in EP 242380.

Non-hydrophobic compounds and especially proteins or peptides may be rendered hydrophobic by coupling hydrophobic groups to them.

The hydrophobic group that can be coupled to the non-hydrophobic compounds are straight, branched, saturated or unsaturated aliphatic chains, preferably having 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 carbon atoms, or hydrophobic amino acids or peptides or other hydrophobic structures such as steroids. The length of the hydrophobic structure is adapted to the size and nature of the protein. As an example, it can be mentioned that a peptide with 10-15 amino acids (foot-and-mouth disease virus) suitably is brought out with two tyrosine at the amino or carboxy terminal end. A protein with a molecular weight of 70,000 daltons demands about 20 hydrophobic amino acids. Testing is made empirically. Thus, one uses especially peptides with 1 to 20 amino acids, preferably 1, 2, 3, 4, 5 amino acids, especially chosen among Trp, Ile, Phe, Pro, Tyr, Leu, Val, especially Tyr; cholesterol derivatives such as choline acid, ursodesoxycholine acid.

These hydrophobic groups must be bonded to a group that can be coupled to the non-hydrophobic protein or compounds such as carboxyl-, amino-, disulphide-, hydroxyl-, sulfohydryl- and carbonyl group, such as aldehyde groups.

As hydrophobic groups that can be coupled are selected preferably carboxyl, aldehyde, amino, hydroxyl, and disulphide derivatives of methan, ethane, propane, butane, hexane, heptane, octane and peptides containing Cys, Asp, Glu, Lys, preferably octanal and Tyr.Tyr.Tyr-Cys,-Asp or -Glu. The hydrophobic groups with a group that can be coupled must be dissolved in water with the aid of for example the solubilising agents and detergents mentioned above or hydrochloric acid, acetic acid 67% by volume acetic acid, caustic liquor, ammonia, depending on what substance is to be dissolved. pH is then adjusted to the neutral direction without the substance precipitating; here it is to make sure that there is not obtained a pH value that denaturates the protein to which the hydrophobic group is to be coupled. Lipid may enhance the solubilisation.

The hydrophobic molecule may be added to the non-hydrophobic compound in the molar ratio of 10:1 to 0.1:1, preferably 1:1.

Hydrophobic groups with a carboxyl group as coupling molecule can be coupled to the protein through water-soluble carbodiimides or composite anhydrides. In the first case the carboxyl group is activated at pH 5 with carbodiimide and mixed with the protein dissolved in buffer pH 8 with a high phosphate content. In the latter case the carboxy compound is reacted with isobutylchloroformate in the presence of triethylamine in dioxane or acetonitrile, and the resulting anhydride is added to the protein at pH 8 to 9. It is also possible to convert the carboxyl group with hydrazine to hydrazide which together with aldehydes and ketones in periodate-oxidized sugar units in the protein gives hydrazone bonds.

The amino groups with nitrous acid can at a low temperature be converted to diazonium salts, which gives azo bonds with Tyr, His and Lys.

The hydroxyl groups with succinic anhydride can be converted to hemisuccinate derivatives which can be coupled as carboxyl groups.

Aldehyde groups can be reacted with amino groups in the protein to a Schiff's base.

Several coupling groups and methods are described in Journal of Immunological Methods (Blair and Ghose 1983), (Conradie, Govender et al. 1983), Methods in Enzymology (Ghose, Blair et al. 1983), and in Analytical Biochemistry (Davis and Preston 1981) which are here incorporated as references.

The proteins, peptides or compounds so produced having received hydrophobic groups are then complex-bonded with glycoside, as described in a), but here the purification steps for removing cell fragments can be omitted.

Hydrophilic proteins having enclosed hydrophobic groups can be rendered hydrophobic by making the hydrophobic groups accessible by gently denaturating the proteins, i.e. with a low pH of about 2.5, 3M urea or at a high temperature above 70.degree. C. Such proteins may be immunoglobulines such as IgG, IgM, IgA, IgD and Ig E. The immunoglobulines can be used as antidiotypic antibodies. The proteins are obtained purified as proteins as described in (b) and then complex-bonded to glycoside as described in (a), the purification steps for removing cell fragments being omitted.

Targeting Molecules for Lipid Containing Particles.

The lipid containing particle may further comprise cancer targeting molecules such as surface antigens from cancer cells, virus surface antigens and influenza antigens.

The present patent application demonstrates that the lipid containing particles such as KGI and BBE particles kills or inhibits growth of a number of different cancer cells at physiological low doses. These types of particles used as adjuvant in iscom and iscom matrix formulations also show good bioavailability, and targeting capacity to lymphatic system in particular to dendritic cells (for references see Morein et al. 2007). To further increase the targeting effect in vivo targeting molecules can be incorporated by various methods. Surface molecules from microbial membranes may be incorporated by hydrophobic interaction as originally described by Morein et al. (1984) and in EP 242380. Other molecules e.g. produced by rDNA technology or synthetically produced can be incorporated as described in WO 2002/080981 and WO 2004/030696.

Such targeting molecules include envelop proteins from viruses such as influenza and respiratory syncytial viruses having affinity to respiratory tract e.g. to target forms of lung cancer, or CTA1 DD being the A1 part of the A subunit of cholera toxin incorporated into KGI or BBE formulations as described by Lycke N. (2004) and by Mowat et al. (2001). CTA1DD is rationally designed of three main components, each contributing complementary effects. CTA1 is the enzymatically active subunit of cholera toxin that is converted non-toxic by separation from the A2 and B subunits. Fused to DD from protein A from *Staphylococcus aureus* it targets B cells. Thus, it is especially suited for B-cells lymphomas. It has already been incorporated into iscoms for targeting B cells for enhanced immune stimulation. In the iscom, besides its targeting effect, it also has an activation and differentiation effect complementing that of the iscom or the KGI or BBE particles. The pure targeting effect is obtained from the DD subunit molecule of protein A from *Staphylococcus aureus* is an alternative for CTA1 as a targeting moiety for BBE or KGI particles possibly complemented with other treatment pharmaceuticals. More generally, mono and polyclonal antibodies can be incorporated into lipid containing particles e.g. into KGI and BBE particles as described in EP 0 109 942 B1, EP 0 242 380 B1 and EP 0 180 564 B1.

Other Additives.

The compositions according to the invention may further comprise a pharmaceutically acceptable carrier, diluent, excipient or additive.

Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in Remington's Pharmaceutical Sciences, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

Pharmaceutical Forms

The lipid containing particle may be administered to man and animal by any route. A parenteral route may be used. The term parenteral as used herein includes subcutaneous injections, intravenous, intramuscular, intradermal injection of infusion techniques, for needle less injection—jet injection as well as oral, aerosol administrations.

The lipid containing particles according to the invention comprising each essentially at least one type of saponin may be administrated in a composition as a mixture or separately in different compositions at the same administration site or at different administration sites at the same or at different times. Different fractions of *Quillaja saponaria* Molina may be used in the different iscom complexes and matrix complexes and in the different compositions.

Generally, the lipid containing particles of this invention are administered in a pharmaceutically effective amount. The amount of the particles actually administered will be typically determined by a physician, in the light of the relevant circumstances, including the condition to be treated, the chosen route of administration, the actual compound administered the age, weight, and response of the individual patient, the severity of the patient's symptoms, and the like.

Doses for human use may vary according to other compounds included. In view of duration of treatment the dose may range from <50 µg to 1 mg or more per day. To best tolerated formulations containing a mixture of 20% KGI and 80% BBE did not cause side effects when administrated in 50 µg doses to 18 g mice, therefore very high doses can be used if that is required.

Kit of Parts

The invention therefore also relates to a kit of parts comprising at least two parts, wherein one part comprises lipid containing particles comprising at least one saponin fraction, which is hydrophobic having a killing effect on cancer cells; and the other part comprises lipid containing particles comprising at least one saponin fraction which is hydrophilic, stimulating and modulating the immune response such as antibody production and cell mediated immunity.

The part comprising lipid containing particles containing at least one saponin fraction which is hydrophobic may also contain particles further having at least one saponin fraction which is hydrophilic.

The compositions and kit of parts according to the invention may also comprise at least one other adjuvant than fractions from *Quillaja saponaria* Molina. These adjuvants may be mixed with the iscom and/or iscom matrix complexes or be integrated into the complexes or be given in free form as such.

Method of Treatment

Throughout this specification and the claims which follow, unless the context requires otherwise, the word "comprise", or variations such as "comprises" or "comprising", will be understood to imply the inclusion of a stated component or group of components but not the exclusion of any other components or group of components.

All publications mentioned herein are hereby incorporated as reference. The invention will now be described by the following non-limiting examples.

Example 1

Formulation of KGI 1 (QHC), KGI 2 (703-matrix ISCOM), KGI 3 (all Quill A fractions including QHA through QHC) and BBE (QHA)

The structure of the *quillaja* saponin in illustrated in FIG. 1.1 showing that the QHA fraction is lacking an alkyl chain present in QHC. The KGI 1 particle is based on QHC in the right area marked in FIG. 1.2. This saponin fraction is more hydrophobic and more lytic than QHA being the basic saponin in BBE on the right area of reversed chromatography marked in FIG. 1.2.

KGI can be formulated from defined *Quillaja* saponin fractions or mixtures of several *Quillaja* saponin fractions. Thus, KGI 1 is made from QHC fraction, KGI 2 is made from a mixture of QHA (7 parts) and QHC (3 parts) and KGI 3 is a mixture of non-separated *quillaja* fractions. Also QHB can be turned into a KGI cancer killing particle. BBE is made from QHA. The proportions can be changed to tailor the desired properties of killing or less cytotoxic properties to emphasize differentiation properties.

Results

The formation of KGI and BBE particles are described in Materials and Methods above and based on work for formulation of ISCOMs (Morein, Sundquist et al. 1984), and later for ISCOMMATRIX Morein et al. 2007. The typical cage-like ISCOM structure of 30-40 nm in diameter was visualized by electron microscopy (EM) (FIG. 1.3). Fractions, after ultracentrifugation, containing cage-like ISCOM structures are observed by EM having a sedimentation coefficient of approximately 20 S (see Materials and Methods)

Conclusion

Particles with various pharmacological effects but with the same morphology are formed and readily envisaged by EM and defined by gradient centrifugation that are used as described in the following examples. These particles can be used for modifying immune response/cancer killing properties and as delivery particle for various molecules in the field of cancer therapy.

Example 2

Lytic Effect on Red Blood Cells (RBC) and Nucleated Cells

It is well known that saponin has cell lytic effect and for this reason it has been tested as candidate for cancer treatment (Wang, Z. P. 2005). *Quillaja* saponin pattern after fractionation by HPLC is shown in FIG. 1.1. In the present invention, QHC used in formulations KGI 1, 2 and 3 particles is highly lytic due to the fatty acyl chain (FIG. 2.1). In contrast, QHA used in formulations BBE, KGI 2 and 3 particles lacks the fatty acyl chain and, therefore, it is virtually non-lytic. RBCs are used to measure the lytic effects of substances on its cell membrane causing a damage allowing the haemoglobin to leak out into the suspension fluid readily determined by spectrometry (see Materials and Methods). The method is sensitive and reproducible. The lytic effect of substances on the cell membranes of nucleated cells has to be tested by a different method. We have used Trypan blue staining. The free KGI have properties of saponin and are lytic by the interaction with cholesterol in the cell membrane resulting in 6 nm hexagonal pores. The dye goes into the damaged cells through these pores in the cell membrane. These pores will instantly cause cell lyses and killing of the nucleated cells. Thus, a lytic concentration of free saponin causes an instant cell death within minutes e.g. 10 minutes has been used to delineate the lytic effect from other cell killing mechanisms requiring hours or days e.g. apoptosis. In the particulate KGI, the saponin is strongly bound to the cholesterol and that prevents the saponin in KGI to interact with cholesterol in the cell membrane preventing the formation of pores and lytic effects.

The nucleated cancer cell U937 and the normal neutrophilic cells from human blood were exposed to free and particulate forms of KGI and BBE.

Results

The results of the haemolytic analyses are summarised in Table 2.1. Free BBE, being the raw material for the BBE particles, did not cause lytic effect in doses up to 50 μg/ml similar to the dose of QHA reported by Ronnberg et. al. (Rönnberg, Fekadu et al. 1995). The BBE particle did not lyse RBC at concentrations up to 100 μg/ml.

QHC, the raw material in free KGI 1 and present in the particulate KGI 1, lysed RBC at a concentration of 5 μg/ml. Free KGI 3 containing saponin fractions (QHA, B and C) lysed RBC at a concentration of 20 μg/ml. The KGI 3 particle did not cause lysis of RBC at a concentration of 100 μg/ml (See Table 2.1).

TABLE 2.1

Cytotoxic and hemolytic activities of various free forms of *Quillaja* saponin and particular forms i.e. KGI and BBE particles

| Saponin fraction | Formulation/ Physical form | Cytotoxicity LC50 (μg/ml) measured by AlamarBlue | | Hemolytic activity (μg/ml) |
|---|---|---|---|---|
| | | U937 | DCs | RBC[1] |
| QHA | BBE | >1920 | >1920 | >100 |
| | Free BBE* | 31.8 | ND | 50 |
| QHC | KGI 1 | 0.8 | 24.3 | 100 |
| | Free KGI 1** | 3.291 | ND | 5 |
| QH-A(7) + QH-C(3) in one particle | KGI 2 | 18.7 | 826 | |
| Non-fractionated | KGI 3 | 14.1 | 625 | 100 |
| Quill A | ***Free KGI 3 | 12.4 | ND | 20 |

*Raw material for BBE;
**Raw material for KGI 1,
***Raw material for KGI 3.

In Table 2.2 the lytic effect of the cells exposed to the KGI formulations for 10 minutes and subsequently stained with Trypan blue is shown. The highest concentration used for treatment of cancer cells has been 50 μg/ml and the nucleated cells were not lysed or killed during this period of time. In contrast, the free form lysed the nucleated cells being 17 μg/ml for neutrophilic cells and 27 μg/ml for U937 cancer cells. The nucleated cells were not killed within 10 minutes not even after one hour of exposure to the particulate KGI 1 (not shown).

TABLE 2.2

Lytic effect of free KGI 1 and particulate KGI 1 on U937 cancer cells on neutrophils detected by trypan blue staining.

| Formulation | U937 cells (μg/ml at LC50) | Neutrophils (μg/ml at LC50) |
|---|---|---|
| Free KGI 1 | 27 | 17 |
| KGI 1 | >50 | >50 |

The cells were incubated with the KGI formulations for 10 minutes

Discussion and Conclusion

It is essential that compounds used for cancer treatment kill cancer cells selectively over normal cells and that the cancer cell killing is efficient in low doses in view of the problem to get high concentrations to the target site in vivo. The lytic effect is characteristic for saponin in free form and not a preferred cell toxic effect for cancer killing. Furthermore, the free form is lipophilic and interacts with the cell membrane at the site of administration, causing local cell destruction and a proportion of the saponin is trapped at that site. The KGI and BBE particles do not lyse the cell membrane of RBCs or nucleated cells in "physiological" doses. As a matter of fact the highest dose tested i.e. 50 μg/ml did not cause lytic or instant toxic effects, while the non-particulate (free) forms of the *Quillaja* saponin caused lytic and cell toxic effect in considerably lower concentrations.

The free form of KGI lyses RBCs and kills nucleated cells within 10 minutes in comparatively low doses. As shown in Example 7, KGI 1 kills the cancer cells at a low physiological dose of 2 μg/ml or even less being less than the lytic or membrane damaging concentrations of the free saponin form. Even high doses of 50 μg/ml of KGI 1 required hours for killing the cancer cells strongly underlining another mechanism involved in cancer cell killing than the lytic membrane damaging effect. To note the cell lytic effect was similar for cancer cells and the normal neutrophilic cells. Thus, it is a great advantage that the particulate forms evade the fast lytic non-discriminatively killing of normal and cancer cells. Moreover, the lytic effect causes local side effects and less bioavailability by trapping the injected substantial amounts of the compounds at the injection site. Thus, it is an innovative feature rendering *Quillaja* saponin particulate for cancer therapy. The particulate form is therefore also a pharmacological delivery system.

Example 3

KGI 1 Selectively Kills Cancer Cells

This example demonstrates that KGI 1 particle selectively kills tumor cells over normal cells measured by the Alamar blue method. A malign monoblast cell line (U937) was selected as tumour cell for comparison with a normal cell i.e. monocyte derived dendritic cells (DCs) (See Materials and Methods). An active saponin component in KGI 1 is QHC (free KGI 1) isolated from commercially available Quill A, which is originating from the tree *Quillaja saponaria* Molina. Free KGI i.e. fraction QHC is highly hydrophobic as compared to the fraction QHA i.e. free BBE as shown in FIG. 3.1 (HPLC chromatogram of Quill A). The QHC differs from QHA by an alkyl chain lacking in QHA explaining the higher hydrophobicity of QHC and its lytic effect (FIG. 3.2).

The tumor cells: monoblast cell lines (THP-1, U937 and U-937-1) and the myeloma cell lines (LP-1 and Jurkat) obtained from the Academic hospital Uppsala, were exposed to KGI 1.

Results

KGI 1, formulated as described in Materials and Methods, kills the tumour as listed above and in Table 3.1. The five listed tumour cell lines were killed by KGI 1 at a LC50 concentration ranging from 0.8-10 μg/ml (Table 3.1 and FIG. 3.1), while the LC50 of the normal DCs is 24.3 (FIG. 3.2). Thus, a 30 times higher concentration of KGI 1 is required for killing the normal cells.

TABLE 3.1

Inhibition of cancer or normal cell growth by saponin formulations

| Cell name | Saponin Dose (μg/ml) in LC50 | | | | |
|---|---|---|---|---|---|
| | Quil A | KGI 3 | free KGI 1 | KGI 1 | BBE |
| Cancer cells | | | | | |
| Jurkat | 0.488 | ND | 10 | 10 | ND |
| THP-1 | ND | ND | 0.939 | 0.875 | ND |
| U937 | 12.426 | 14.073 | 3.219 | 3.068 | >1920 |
| U937-1 | ND | ND | 1.761 | 1.601 | ND |
| LP-1 | ND | ND | 1.897 | 1.998 | ND |

TABLE 3.1-continued

Inhibition of cancer or normal cell growth by saponin formulations

| Cell name | Saponin Dose (μg/ml) in LC50 | | | | |
|---|---|---|---|---|---|
| | Quil A | KGI 3 | free KGI 1 | KGI 1 | BBE |
| Normal human cells | | | | | |
| DC | ND | 625 | ND | 24.322 | >1920 |
| Neutrophils (acute lysis) | ND | ND | 28.551 (5 minutes) | >50 (5 hours) | ND |

Discussion and Conclusion

The inventors have identified a *Quillaja* saponin fraction that in the particulate form, KGI 1, selectively kills tumour cells. In this case the monoblast cell U937 was killed at a concentration that is a 30-fold lower than a concentration required for killing the normal cell. The high killing effect can be localised to a hydrophobic fraction of a reversed phase diagram of *Quillaja* saponin. In contrast, the more hydrophilic fraction QHA (FIGS. 1.1 and 1.2) is not killing cancer or normal cells at relevant doses.

Thus, KGI 1 is a candidate for cancer therapy as will be further substantiated in the following examples.

Example 4

BBE is Non-Toxic for Nucleated Cells

The comparatively hydrophilic fraction QHA (free BBE) from a reversed phase diagram (FIGS. 1.1 and 1.2) was incorporated into the BBE particles and tested for their killing effect on cancer or normal cells and found non-cytotoxic (FIGS. 4.1 and 4.2).

Results

BBE particles did not kill cancer (FIG. 4.1) or normal (FIG. 4.2) cells at relevant doses i.e. at concentrations tested up to 1920 μg/ml.

Discussion and Conclusion

This example demonstrates that a BBE particle is virtually free of cytotoxicity i.e. well accepted by both normal and tumour cells. BBE particle does not kill the tumour or normal cells at any concentration tested up to 1920 μg/ml (FIGS. 4.1 and 4.2). One difference is that the saponin in BBE lacks an aliphatic chain also explaining the low lytic effect of the free form of the active substance QHA (see Example 2, Tables 2.1 and 2.2). The BBE particle will be useful to moderate or modulate the activity of KGI particle in view of its modulatory effect e.g. by stimulating cytokine production.

Example 5

BBE Blocks the Cell Killing Effect of KGI

This example shows that BBE blocks the killing of KGI 1. The most prominent difference is that the saponin in KGI 1 has an alkyl chain while the saponin in BBE lacks that chain (for more details see examples 1, 2 and 4)

Results

A constant concentration of KGI 1 of 77 μg/ml was incubated with an increasing concentration of BBE and applied on U937 cancer cells. The cell toxic effect of KGI 1 was blocked at a ratio of 10:1 (KGI 1: BBE). The blocking effect is likely to be mediated by receptors as revealed by the curve in FIG. 5.1.

The blocking effect is efficient in view of the constant high KGI 1 concentration of 77 μg/ml we used, considering that its LC50 on U937 cells is just 0.8 μg/ml.

Discussion and Conclusion

The inventors have identified a substance in the form of KGI 1 particle that selectively kills tumour cells. They have identified another substance formulated as BBE particle that blocks the killing effect by KGI 1, both on tumor cells and on normal cells (not shown). I.e. a tumor killing system is created, which can be effectively moderate toxicity if that should occur. It should be noted that the active substances QHC and QHA in this example are present in different particles namely KGI 1 and BBE. It is likely that the blocking receptor promoting cancer cell death is different from the receptor promoting the activation and differentiation of normal and cancer cells.

Example 6

The KGI and BBE are Delivery Systems, the Effect of Presentation of Active Substances in One or Two Different Particles is Analysed in Normal and Cancer Cells Example 5 shows that active substance QHA in a separate BBE particle blocks the cell toxic effect of KGI 1 containing another active saponin i.e. QHC. This blocking effect is likely due to blocking via one or more receptors.

The KGI 2 harbors the two active saponin substances QHC, the active substance of KGI 1, and QHA being the active saponin of BBE. This example illustrates that these two components in one and the same particle combines and moderates the effects of each of the components. The example also shows that the same components co-administered in separate particles moderates and modulates the response of the exposed cells.

KGI 2 like particles harbored different proportions QHA/QHC in the proportions 7:3, 7.5:2.5 or 9.5:0.5 prepared as described for KGI 2 (703) with different proportions of the starting material. The cell survival was measured by Alamar-Blue (See Materials & Methods).

In the experiment illustrated in FIG. 6.2 the KGI 2 (703) was incubated with U937 cancer cells for 48 hours and similarly with human immature DCs (FIG. 6.3).

Normal mammalian cells have various tasks to sustain the animal or human life. One DC population originates from monocytes. In this example human peripheral blood cells have been treated with IL-4 and GMC-SF to obtain a monocyte derived immature DC population obtained from 3H biomedical (Uppsala, Sweden). For detailed information used in this example see Materials and Methods. This example demonstrates that various KGI and BBE formulations activates immature human DCs to mature and express a DC marker CD86 being a molecule of activated DCs communicating to lymphocytes to differentiation and activation to be effector cells.

The different KGI and BBE formulations are KGI 1 containing only KGI 1; KGI 2 prepared from 70% QHA (raw material of BBE) and 30% of QHC (raw material for KG) 1) in one and the same particle; KGI 3 containing a mixture of *Quillaja* saponin fractions in the form of Quill A; only BBE and the BBE+KG) 1 formulation is composed of 80% of BBE particles and of 20% KGI 1 particles i.e. each compound in separate particles. Initial studies have shown that the treatment concentration should be 1 µg/ml cell culture fluid for KGI 1, KGI 2 and KGI 3, while for BBE and BBE+KGI 1 the concentration should be used at 10 µg/ml. For details see Materials and Methods.

Results

The KGI 2 like formulations, with the different ratios of QHA:QHC fractions ranging from 7:3, 7, 5:2.5 incubated for 2 days, killed the U937 cancer cells at the concentrations from 20 to 100 µg/ml. The dilution of the active QHC fraction with the QHA fraction to 0.5 to 9.5 completely abolished the cytotoxic activity within the incubation time of 48 hours (FIG. 6.1). These results should be compared with those given in Example 5.

A second experiment demonstrates that KGI 2, combining QHA and QHC saponin fractions in one and same, the particle in the proportion QHA:QHC 7:3 kills the U 937 tumour cell at LC50 of 18.7 µg/ml (FIG. 6.2), which is a 23 times higher than the LC50 of KGI 1. The normal human DCs required 44 times higher concentration of KGI 2 for cell death than the U937 cancer cells i.e. LC 50 of 826 µg/ml (FIG. 6.3).

In Table 3.1, the cancer cell killing effect by different KG) particles on various cancer cells, measured by the Alamar-Blue method or Trypan blue for the normal human neutrophilic cells, are summarized. In general, it can be concluded that several different cancer cells are sensitive to KGI formulations and even more sensitive than the U937 cells. The U937 cells in this application were used as a model for more in fundamental studies.

An activating and differentiating activity is shown FIG. 6.4. KGI 2 in the low physiological dose of 1 µg/ml, indicated the highest proportion CD86 positive cells (67.3%) indicating a synergistic effect between KGI 1 and BBE components in one and the same particle i.e. the KGI 2 particle. It also shows that KGI and BBE particles are carrier-delivery particles, i.e. KGI 2 delivers 2 components.

BBE induced the same proportion of CD 86 positive cells as LPS, while the formulation BBE+KGI 1 induced 65.8%. The latter two formulations required a 10-fold higher dose i.e. 10 µg/ml than KGI 2.

Discussion and Conclusion

KGI 1, KGI 2 and KGI 3 like formulations are delivery systems that combine two and potentially more different components with different properties. In this example, two different properties were combined resulting in a completely different cancer killing effects. Simply, mixing the two different compounds i.e. KGI 1 and BBE confined to different entities (particles) as described in Example 4 moderate the activity by blocking. The combination of the two substances in one and the same KGI particle (KGI 2) reduced toxicity in a dilution manner i.e. reduction of the density of KGI 1 ligands since blocking cannot be achieved with different components in one and the same particle. The mentioned effects were recorded in both cancer and normal cells. Although the toxicity of KGI 2 for a cancer cell was reduced many folds compared to that of the KGI 1 particle the margin of toxic effect on a normal human cell (DCs) to a cancer cell (U937) increased from a 30-fold (KGI 1) to a 40-fold (KGI 2). It is conceivable that the dilution effect is caused by lower avidity as the number of ligand-receptor interactions inducing the cell killing is reduced. The cytotoxic effect is most probably exerted by a different ligand-receptor constellation than the one mediating the blocking effect. In the KGI 2 particle or other like particles, it is possible to combine the modulating capacity of BBE and the killing effect of KGI 1 by increasing the LC50 from 0.8 µg/m of KGI 1 to 18.7 µg/ml in KGI 2 and still keep or increase a high margin between toxicity of cancer cells and normal cell e.g. 40 fold difference. That is likely to have a clinical bearing in vivo. The cancer cell killing effect of KGI 1 is linearly decreased by the blocking effect of BBE but the differentiation capacity exerted by both particles is not substantially changed as can be read from the experiments so far done. The flexibility of these findings makes it possible to tailor toxicity and activation-differentiation of cancer cells to normalized cell behavior with a programmed ending with apoptosis. It is noteworthy, that both formulations i.e. two substances in the same particle or the two substances in separate particles are likely to have clinical value. For instance, KGI 1 kills the cancer cells at a too low concentration that may hamper other properties such as differentiation, activation of cancer cells ending with programmed cell death-apoptosis, which may have bearings on bystander effects i.e. effects on adjacent cells not being directly exposed (see example 7). For example, it is well established that in the immune system killed DCs release components that cross stimulate adjacent DCs.

Apoptosis (see Example 7) is less a dramatic for the individual than cell death by necrosis, thereby evading cell toxic affects that cause illness in the treated individuals. Apoptosis of cancer cells is, therefore, attractive in cancer therapy. In this context it can be anticipated that killed cancer cells release immunogenic components that can initiate immune protection under the influence of active immune enhancing components like those harbored in KGI and BBE containing particles. Thus, the KGI particle is a delivery system that opens the possibility to tailor cell death or to integrate other substances with various anti-cancer activities. Such substances should, preferably, act over other principles as e.g. taxol killing cells over damaging the cytoskeleton or vitamin A or D promoting differentiation over different mechanisms than KGI or BBE particles. The KGI particle demonstrates a delivery capacity that is not limited to the components used in this example. In conclusion, the various KGI or KGI in combination with other compounds e.g. BBE in free or particulate forms selectively kill cancer cells over normal cells (Table 3.1).

The KGI 1 formulation activate—stimulate the cancer cell U937 to produce IL 8 and apoptosis but not to cell death characterised by necrosis (see Example 7). Other KGI formulations like KGI 2 and 3 require much higher concentration to kill normal and cancer cells and still there is a 30 to 40 fold safety margin for the normal cells (see examples 5 and 6). In this example it is illustrated that a high proportion of normal immature DCs is stimulated to mature DCs, expressing CD86. Most interestingly it is found that by combining the active compound QHA or BBE with QHC being the saponin component in KG) 1 in one and the same particle a synergistic effect was recorded, i.e. the low dose 1 μg/ml of KGI 2 induced the highest proportion of CD86 positive cells. BBE requiring 10 μg/ml by its own now was used at a concentration of 0.8 μg/ml cell culture fluid of the active compound combined with 0.2 μg/ml of the active KGI 1 compound in KGI 2 formulation. Both of these active components were considerably lower than that required by each of the components used by its own. That is, the concentration of BBE compound was reduced more than a ten-fold and that of the active KGI compound was reduced a five-fold in the KGI 2 particle providing increased effect. The KGI 3 containing a number of *Quillaja* saponin fraction did not in this example induce CD86 expression, it rather inhibited that. More experiments are required to confirm if there is an inhibitory effect of KGI 3 as regard to expression of CD86.

In conclusion an unexpected synergistic effect measured by maturation of human DCs is shown when two components in the KGI 2 particle interacts with cells emphasizing valuable prospects for the KGI and BBE particles as carrier systems targeting cells via receptors. Since the cancer killing effect by the KGI and/or BBE particles is proposed to act via activation and differentiation, it should be possible to analyse on normal cells. It should be noted that cancer cells are very different and a cancer cell killing system where the targeting properties can be changed is giving rise to new possibilities for cancer treatment.

Example 7

Analyses of KGI 1 Cancer Killing Effect by Applying Different Detection Systems

*Quillaja* saponin in the particulate form KGI kills cancer cells in 30 to 40-fold lower concentrations than normal cells (Example 3). In this example, cancer cell death has been analysed by several methods including Trypan blue staining, enzymatic metabolic inhibition by the AlamarBlue method, by necrotic changes visualized by propidium iodide staining and by apoptosis via Annexin V staining as described in details in Materials and Methods. The Trypan blue staining of cells in connection with treatments is informative to establish the number of cells and the viability was determined up to 9 days (FIGS. 7.1, 7.2). Low dose of KGI 1 (2 μg/ml) caused cancer cell death after a longer period, while a high dose (25 μg/ml) killed within a shorter period (FIG. 7.3) and triggered faster apoptosis (FIG. 7.6). In this example, the cell death measured by the Trypan blue method was correlated to the programmed cell death i.e. apoptosis following the exit of cells from the cell cycle. The cell cycle is the basis for cell replication, and it is significant for cancer cells that they remain in the cell cycle for a continuous replication. An exit from the cycle means that the cells can start activation towards production in this case cytokine production (Example 10) and finally progress to a programmed cell death as demonstrated in this example. We have used a Thymidine kinase (TK) test to indicate whether the treated cells are in the replication phase i.e. in the cell cycle or escaped from the cycle (Example 9) and entered the pathway leading to production capacity and finally apoptosis.

The capacity of KGI 1 to kill the cancer cell U937 is analysed by the Trypan blue staining method (see Materials and Methods) in following experiments:

The U937 cells were seeded in micro-titre plate with 2 μg/ml KGI 1. In one set of cultures, the cells were exposed to KGI 1 continuously for 9 days (FIG. 7.1). The cell number was adjusted to $1 \times 10^6$/ml at every 3 days in fresh medium containing the same concentration of KGI 1. At each occasion the accumulated number of cells was calculated.

In a second set of cultures, the KGI treatment was terminated after 3 days by replacement of the medium with no KGI 1 (FIG. 7.2). The cell number was adjusted to $1 \times 10^6$/ml at each occasion when the medium was changed. The accumulated number of cells was calculated. U937 cancer cells were exposed to the high dose of 25 μg/ml of the free or particle forms of KGI 1 and sampled as indicated in the FIG. 7.3. The cells were stained with trypan blue and the viability was counted by microscopy. Cell viability is expressed as percent of the viable cells of the cell control.

To compare cytotoxicity, U937 cancer cells were exposed to the low physiological dose of 2 μg/ml of free or particle forms of KGI 1 as indicated in the FIG. 7.4. The cells were stained by Trypan blue. Viability is expressed as percent of the viable cells of the cell control.

U937 cancer cells were exposed for 12 days to the low doses of 0.5 μg/ml or to 2 μg/ml of KGI 1 as indicated in the FIG. 7.5. The number of cells was counted after staining by the Trypan blue method.

The capacity of the particulate KGI 1 to induce apoptosis was analysed in U937 cancer cells. The cells were exposed for 120 hours to KGI 1 at the concentrations of 2 µg/ml or to 25 µg/ml (FIG. 7.6). The numbers of Annexin V positive cells (FIG. 7.6) and necrotic i.e. propidium iodide (PI) stained cells (FIG. 7.7) were determined simultaneously by FACS (see Materials and Methods). The U937 cancer cells were exposed for 120 hours to KGI 1 at the concentrations of 2 µg/ml (M2) up to 50 µg/ml (M50).

In FIG. 7.8, U937 cells were exposed for 120 hours to KGI 1 at concentrations from 2 µg/ml up to 50 µg/ml. The cells were sampled and stained with propidium iodide and Annexin V as indicated in the figure. The proportions of affected cells were determined by FACS. Details are given in Materials and Methods.

Results

Viability of U937 cancer cells after prolonged treatment with KGI 1 are shown in FIGS. 7.1 and 7.2. An interrupted treatment of cancer cells with a low physiological dose of 2 µg/ml of KGI 1 was as efficient for inhibition of proliferation and killing the cancer cells as the continuous treatment. The cell number had decreased to virtually no viable cells after 9 days of incubation. The number of non-treated cells increased from 1 million/ml to 3 million/ml during cultivation for 3 days. The number of treated cells were reduced to less than $0.5 \times 10^6$/ml after 3 days of culture and decreased further during the 9 days of culture (FIGS. 7.1 and 7.2).

The high dose of 25 µg/ml of the free form of KGI 1 i.e. QHC fraction of Quill A killed the cells fast i.e. within 3 hours, while that concentration of the KGI 1 particle required longer time i.e. 24 hours to kill a high proportion of the cancer cells.

The low physiological dose 2 µg/ml of the free form of KGI 1 i.e. QHC fraction of Quill A did not kill the cells within 60 hours, while that concentration of the KGI 1 particle started to kill the cancer cells after 24 hours of culture and continued during the experimental culture period of 60 hours, when the cell viability had decreased to 20%. At this concentration the free non-particulate form failed during the culture period of 60 hours to reduce the number of cancer cells. This concentration is not cell lytic.

The very low dose of 0.5 µg/ml KGI 1 particles reduced the cell number compared to the non-treated cells, while the physiological dose of 2 µg/ml of KGI 1 particle killed all cancer cells within the 12 days of culture (FIG. 7.5).

The induction of programmed (apoptotic) cell death is shown in FIG. 7.6. The concentration of 2 µg/ml of KGI provoked increased population of apoptotic U937 cells with a peak level after 24 hours of exposure. The higher concentration i.e. 25 µg/ml of KGI further increased the proportion of apoptotic cells with peak levels after exposure for 12 and 24 hours.

The Induction of Necrotic Cells (FIG. 7.7).

In contrast to the effect of KGI 1 particles on the induction of apoptosis there was no effect on the necrotic cell death. That is there was no difference in the proportion of necrotic cells between cells treated with various doses of the particulate KGI 1 and control cells not exposed to KGI 1.

FIG. 7.8 shows U937 cancer cells treated with KGI 1 over time stain both for propidium iodide (PI) and Annexin V during experimental period for 120 hours at the concentrations of 2 µg/ml up to 50 µg/ml. Increasing concentration and over time induced an increased population of cells stained for both necrotic and apoptotic effects. The controls showed the least proportions of cells stained both for apoptosis and necrosis. Initially, the KGI 1 treated cells stained mainly and only for Annexin V, but over time the cells become necrotic and double stained.

Discussions and Conclusion

A low dose (2 µg/ml) of KGI 1 treatment of U937 cells reduces drastically the number of cells after 3 to 6 days. After 12 days there is virtually no viable cancer cells left. A high dose of KGI (25 µg/ml) kills all cancer cells within 36 hours. In example 3, we have shown that U937 cancer cells are 30 to 40 times more sensitive than normal cells. Once the killing of cancer cells is induced (see FIGS. 7.2 and 8.1), there is no return since the removal of the KGI 1 from the culture does not stop the progress to cell death (see also example 4). Normal cells have a destiny of a programmed death (apoptosis) that causes no adverse symptoms. In this example, we could show that prominent apoptosis was induced by KGI 1. The proportion of apoptotic cells increased up to 24 hours of exposure. A low dose of 2 µg/ml of KGI 1 provoked the most prominent apoptosis after incubation for 24 hours.

Over time, the proportion of Annexin V positive cells decreases and the proportion of cells that stains for both Annexin V and PI increased. KGI 1 treatment provoked considerably larger double positive cell population than non-treated cultures. The double stained cell population originates from either necrotic or apoptotic cells. Initially, there were only a low proportion of PI positive cells equal in both treated and non-treated cell populations. It is, therefore, likely that the high proportion of double positive cells after KGI treatment originates from an initially apoptotic population.

The ceased TK activity after exposure to KGI 1 (Example 9) coincides with the effect that U937 cancer cells start production of cytokine IL-8. The IL-8 production was used as an indicator for activation of the cancer cells to a production phase provoked by KGI 1 as shown in example 10. The stimulatory effect is close to the concentration where KGI 1 is killing the cancer cells. An innovative and interesting scenario is that the stimulatory effect takes the KGI 1 treated cells out of the cell cycle towards a production phase to the unavoidable destiny of normal producing cells to the final programmed apoptotic death. To note, KGI formulations have never been able to stimulate cell proliferation. A cancer cell killing process has a strong advantage over cancer cell killing by cytostatica or irradiation being symptom free or at least the side effects are minimized.

Example 8

KGI 1 causes cancer cell death that does not allow the cells to revert to uncontrolled replication Drugs used for cancer treatment may have an initial good effect, but after a continued treatment the cancer cell killing effect may revert and the cells start uncontrolled replication. Thus, it is essential that treated cancer cells do not revert to an uncontrolled cell proliferation. Example 7 shows that KGI 1 kills cancer cells including a mechanism of apoptosis. This example demonstrates that after a prolonged culture of the U937 cancer cells treated with KGI 1, the cells do not revert to replication, more significantly, even after an interrupted treatment with a low physiological dose.

U937 cells were cultured with 0.5 µg/ml or with 2 µg/ml of KGI 1 particles over a period of 12 days and the cell survival rates were compared with that of non-treated cells cultured under the same conditions by staining with Trypan blue as described in Materials and Methods.

In the following experiment (FIG. 8.2), the treatment of the synchronized U937 cells with a concentration of 2 µg/ml of KGI 1 was interrupted after culture for 72 hours by replacing the medium containing KGI 1 with fresh medium without KGI 1. Every three day, the medium was changed to promote the cell growth. After culture for 12 days, the number of viable cells was counted after staining with Trypan blue.
Results
The number of U937 cancer cells continuously exposed to KGI 1 at a concentration of 2 µg/ml is first increased and then steadily decreased from a time point between 1 and 3 days. At the end of the experimental period of 12 days, less than 10% of live cells were recorded (FIG. 8.1). After the treatment with 0.5 µg/ml of KGI 1 there was an initial increase of the cell number followed by a reduction to half of that from day 3 after the starting point and then the number of cells was significantly lower than that of the non-treated control cells. The control cells reached a cell number three times of that from the start. Thus, following treatment of the cells with KGI 1 after an initial period of replication, the number of viable cells decreased following with the low physiological concentrations of KGI 1.

FIG. 8.2. shows that KGI 1 inhibits proliferation and kills the cancer cell U937, and the cells do not revert to proliferation during the 12 days of culture even after removal of KGI 1 on day 3.
Discussion and Conclusion
Example 3 presents and discusses the cancer killing effect exerted by KGI 1. From this example, we can draw the conclusion that the cells treated with a low and physiological dose of 2 µg/ml KGI 1, even after interrupted treatment, do not revert to cell proliferation.

The treatment with 0.5 µg/ml of KGI 1 reduced the cell number significantly compared to that of the non-treated control cells. After an initial period of replication, the number of viable cells decreased. It is likely that the viable cell count in the cultures treated with the lower concentration (0.5 µg/ml) of KGI 1 indicates surviving cells in the absence of replication. In conclusion, U937 cancer cells exposed to KGI 1 at low physiological concentration do not revert to uncontrolled replication, but the cell number steadily decreases.

Example 9

Cancer Cells Treated with KGI 1 Exit the Cell Cycle

Example 7 demonstrates that KGI 1 kills cancer cells including a process of apoptosis, and example 8 shows that the killing of cancer cells is irreversible. Example 10 shows that KGI 1 guides the U937 cells to enter a production phase without adding a cell-activating or differentiating agent like phorbol-12-myrestate-13-acetate (PMA) as required for other agents (Baldridge, Cluff et al. 2002). The cell cycle governs the cell replication (FIG. 9.1). In the S-phase, being early in the cycle, the DNA of the daughter cells is built up. One of the DNA building blocks is the nucleotide thymidine. Thymidine requires the enzyme Thymidine kinase (TK) for its phosphorylation. Thus, this enzyme has to precede the S-phase to be available. Here we use TK activity to explore whether KGI 1 influences the cell cycle of U937 cells and if KGI 1 treated cells stay in or exit the cycle. The persistence of KGI 1 treated cells in the cell cycle is analysed in this example by detecting the TK-activity over time, by correlating the TK activity with the inhibition of cancer cell-metabolism (recorded by the AlamarBlue test), killing (measured by Trypan blue exclusion staining) and in the discussion with apoptosis. The cell metabolism, replication and TK activity of non-treated cells were used to recording the cancer cells remaining in the cycle.

One million/ml U937 cells were seeded in micro-titre plate for the experiments carried out in this example. Attempt to synchronize the U937 cells in the cell cycle was done by starving the cells for 22 hours via reduction of the concentration of fetal calf serum in the cell culture medium from 10% to 0.5% as detailed in Materials and Methods. The TK activity was measured and comparisons were done between cells treated with particulate KGI 1 at the concentrations of 2 µg/ml or 25 µg/ml and non-treated cells. Measurements were done at intervals up to 5 days as described in the FIGS. 9.2 and 9.3 and effects are detailed in results. In FIG. 9.4 the reduction of TK activity, measured in cell lysate, was compared after treatment of the U937 cells with particulate KGI 1 with that at the same concentrations of free i.e. non-particulate KGI 1. Samples were tested in cell lysate daily for 120 hours after treatment of $10^6$/ml of the cells treated with 2 µg/ml (M2), 10 µg/ml (M10), 25 µg/ml (M25) 50 µg/ml (M50). In FIG. 9.5 the TK activity was measured in the cell culture fluid after the same treatment with free and particulate KGI 1 as shown in FIG. 9.4.

In FIG. 9.6. the TK activity was analysed on synchronized U937 cancer cells exposed to 2 µg/ml of KGI 1 for 0, 2, 8, 18 and 24 hours. The non-treated controls were sampled at 0, 8 and 24 hours.

FIG. 9.7. Synchronized U937 cells were exposed to 2 µg/ml of KGI 1 for 2, 8, 18 and 24 hours. The controls were sampled at 8 and 24 hours. The viable cells were counted after staining with Trypan blue.

FIG. 9.8. The cell metabolic inhibition (AlamarBlue) and cell killing (Trypan blue) were measured on synchronized U937 cells after treatment for 24 hours with 0.5 µg/ml or 2 µg/ml of particulate KGI 1 or free KGI.
Results
The TK activity of treated cells was reduced compared to that of non-treated controls during the 5 days of culture. Reduction of the TK activity after treatment with the high dose of 25 µg/ml of KGI 1 is prominent after 24 hours and for the low dose of 2 µg/ml of KGI 1 after 48 hours (FIG. 9.2). The TK activity of treated cells is also recorded as percent of the non-treated cells FIG. 9.3. After 3 days no TK activity was detected from cells treated with 25 µg/ml of KGI 1. The cell treatment with low dose of 2 µg/ml of KGI 1 reduced the TK activity to 10% after 5 days.

FIG. 9.4 shows that a low physiological dose of 2 µg/ml of KGI 1 causes a prominent reduction of TK activity after exposure of the cancer cells for 48 hours, but being most prominent after 72 hours of exposure. The reduction of TK activity is less prominent after treatment with free KGI 1. Reduction of the TK activity after treatment with the high doses of 25 or 50 µg/ml of KGI 1 is prominent earlier i.e. after exposure for 24 hours. Cells treated with the high doses of free KGI 1 i.e. 25 and 50 µg/ml abolished all detectable TK activity at all time points during the 6 days of culture, but TK activity was, instead, detected in the culture medium (FIG. 9.5) indicating cell membrane damage. To note, these concentrations of free KGI 1 have lytic effect (Example 2, Table 2.1). In contrast particulate KGI 1 did not release detectable amounts of TK to the cell culture fluid.

FIG. 9.6 shows that KGI 1 at a low physiological dose of 2 µg/ml reduces TK activity of synchronized U937 cancer cells recorded in cell samples treated for 18 and 24 hours i.e. before entering into the replication phase in the second cell cycle. No inhibition of TK activity took place with the low dose during the first 8 hours.

FIG. 9.7 shows that a physiological low dose of 2 µg/ml of KGI 1 inhibits proliferation and reduces the number of cancer cells detected after 18 hours of exposure measured as cell viability in culture coinciding in time with reduced TK activity as shown in FIG. 9.6.

Particulate and free KGI 1 at a concentration of 2 µg/ml reduced the cell viability and metabolism after the treatment of U937 cells for 24 hours, which was measured in this experiment (FIG. 9.8). The concentration of 0.5 µg/ml of particulate or free KGI 1 reduced the cell viability after the treatment period of 24 hour. The inhibition of cell metabolism by 0.5 µg/ml was more prominent after treatment with KGI 1 than after that with the free KGI 1. In general particulate KGI 1 was in more efficient inhibitor of cancer cell growth both measured by cell metabolism and viability. There is also a good correlation between the number of viable cells and cell metabolic activity.

Discussion and Conclusion

U937 cancer cells treated with a low dose of 2 µg/ml of KGI 1 did not reduce the TK activity when measured in non-synchronized cells after 24 hours but after 48 hours reflecting the KGI 1 inhibitory effect is late in the first cycle (FIGS. 9.2-9.5). In synchronized cells the inhibition of TK activity appears earlier (FIG. 9.6). TK activity is early in the cell growth cycle. A high concentration of 25 µg/ml of KGI 1 reduces the TK activity earlier. Most likely, the KGI 1 treatment makes the cells to exit the cell cycle. In general, the TK activity ceased after 5 days of treatment with KGI 1 in physiological doses. It should be noted that the measured TK activity includes the sum of newly produced Thymidine kinase and residual Thymidine kinase that is expected to last for some time from the previous cycles. The high dose of KGI 1 of 25 µg/ml reduced the TK activity to 50% recorded after incubation for 24 hours indicating that a high dose interferes with cell growth earlier in the cell growth cycle. The reduced TK activity is reflected and coincides in time with metabolic inhibition (AlamarBlue analysis), and reduced number of viable cells measured by Trypan blue staining (FIGS. 9.7 and 9.8). The decreased cancer cell number after KGI 1 treatment for 18 hours in synchronized cell cultures indicates an inhibitory effect by KGI 1 in the first cell cycle.

Apoptotic cancer cell killing (Example 7) is provoked towards 24 hours and the apoptotic killing coincides with the early effects of high and low doses of KGI 1 on the TK activity. It should be noted that in the early phase of KGI 1 induced cancer cell killing, the number of necrotic cells did not exceed that of non-treated cells (see Example 7). The conclusion is that the accumulated cell number stained by both PI (necrosis) and Annexin V (apoptosis), to a great extent, originates from apoptotic cells provoked by KGI 1.

However, it cannot be ruled out that the early effect of higher doses of KGI 1 has a direct influence on the TK production preceding the S-phase of the cell cycle.

The cancer killing effect of free KGI 1 is particularly prominent in the higher concentrations tested i.e. 25 µg/ml and 50 µg/ml, but at these concentrations, the TK was released to the culture medium (FIG. 9.4) indicating damage of the cell membrane. At lower concentrations, the free form had lower capacity to reduce the TK activity than the particulate KGI 1.

The early cancer killing effect of KGI 1 by the high doses of 25 µg/ml and 50 µg/ml i.e. before 24 hours points to a different mechanism exerted in the early phase of the cell cycle than the low concentrations of 2 µg/ml and 10 µg/ml that apparently is affecting the cells after the production of TK. The higher concentrations of 25 µg/ml and 50 µg/ml of particulate KGI 1 are not lytic as it is for the free form of KGI 1 i.e. QHC fraction of Quill A (Example 2).

In conclusion, the particulate KGI 1 kills cancer cells without causing a primary necrosis even at high doses. TK activity is interrupted almost simultaneously with apoptotic death and coincides with the inhibition of cell metabolism measured by AlamarBlue and cell killing measured by Trypan blue staining. KGI 1 has no lytic effect at the doses tested. No reversion is noticed at prolonged culture. The cancer cell killing effect by KGI 1 follows the concept of an exit from the cell cycle leading to an activation and production phase and a final apoptosis. In contrast, the free form of KGI 1 i.e. QHC fraction of Quill A kills besides apoptosis, by necrosis and at high doses by lytic effect. Free KGI 1 is less efficient in cancer cell killing when used in low physiological doses. The high efficient concentrations of free KGI 1 provoke side effects.

Example 10

KGI Formulations Induce U937 Cells to IL-8 Cytokine Production

It has been shown that the lipopolysacharride (LPS) compound stimulates U937 cells to cytokine production (IL-8) using doses exceeding those of KGI 1. In another experiment Baldridge et al. (Baldridge, Cluff et al. 2002) claimed that of aminoacyl glucosaminid 4-phosphate (APG) had such stimulatory effect on 0937 cells measured by cytokine production. However, in order to achieve that capacity, the culture had to be pretreated with phorbol-12-myrestate-13-acetate (PMA) to facilitate that differentiation and activation. This example shows that KGI 1, 2 and 3 do not require an additional activation—differentiation compound to enter a cytokine production phase and the dose of KGI formulations required is low. Moreover, Examples 7 and 9 shows that KGI 1 takes U937 cancer cells out of the cell replication cycle in which cancer cells are trapped unless treated with KGI 1. Examples 7 and 9 also show that KGI 1 takes U937 cells to apoptosis. Apoptosis is a final step for normal cells when they exhausted their tasks e.g. for production of cytokines. In this example, the capacity of the three KGI formulations, i.e. KGI 1, 2 and 3 to induce U937 cells to produce cytokine IL-8 is tested.

KGI 1, 2 and 3 were formulated as described in Materials and Methods and added in concentrations shown in FIGS. 10.1, 10.2 and 10.3 to U937 cells at a density of $10^6$/ml in micro-titre plate. After incubation for 2 days at 37° C., IL-8 was determined in the supernatant. The production of IL-8 at LC50 was also calculated as shown in these figures.

Results

The production of IL-8 was 781 µg/ml at LC50 for KGI 1 (FIG. 10.1), 881 µg/ml for KGI 2 (FIG. 10.2) and 916 µg/ml for KGI 3 (FIG. 10.3). The different KGI formulations cause also different degrees of cytotoxicity as shown in these figures.

Discussion and Conclusion

U937 cells do not spontaneously produce cytokines. Although, Baldridge et al. (Baldridge, Cluff et al. 2002) claimed that certain APGs at high dose can stimulate U937 cells to cytokine production that required pretreatment of e.g. a high dose of the (MPA). This example shows that the KGI formulations do not need a MPA or similar treatment to enter a cytokine production phase. Moreover, Example 9 shows that KGI 1 takes L1937 cancer cells out of the cell replication cycle, in which cancer cells are trapped unless treated with KGI 1. Example 4 shows that KGI 1 takes U937 cells to apoptosis. Apoptosis is a final step for normal cells when they exhausted their tasks e.g. for the production of cytokines. In this example, the capacity of the three KGI formulations, i.e. KGI 1, KGI 2 and KGI 3 to induce U937 cells to produce cytokine 8 is tested. In conclusion, the different KGI formulations do induce cytokine 8 production proceeding Apoptosis. Also BBE induces IL-8 production (not shown).

Example 11

Acute Toxicity of KGI 1 and BBE in Mice

Drugs intended for cancer treatment mostly cause side effects together with poor bioavailability being the most common cause that potential compounds for cancer treatment do not progress into clinical trials or do not reach the market. *Quillaja* saponin has been used in more than 50 years in free form in animals. It is well known that local reactions in form of swellings, redness and tenderness even necrosis could appear as side effects limiting the dose. Side effects of that kind were not recorded after the incorporation of QHC into Iscoms and Iscom matrix formulations, when similar doses were used. Ten µg of free QHC induces local reactions injected intramuscularly in mice but not incorporated into Iscoms or KGI formulations. It is also well recognized that the free saponin interacts with cholesterol and causes damage in the cell membrane avoided by the blocking effect of the incorporated cholesterol binding to the saponin in the Iscom and KGI formulations. In this example, systemic toxicity of KGI 1 and BBE was tested in BALB/c mice. The acute toxicity was tested after subcutaneous administration of KGI 1 and BBE in BALB/c mice as described in Materials and Methods. The mice were recorded for four days. The results of the testing are summarized in Table 11.1 and the scoring for degree of lethargy is described in Table 11.2.

In the example the general toxicity of KGI 1 and BBE is explored and compared to the free forms of the integrated saponin i.e. fraction C of *Quillaja* saponin integrated into KGI 1 and fraction A integrated into BBE. The doses 10, 30 and 50 µg of KGI 1, 50 and 100 µg of BBE were injected subcutaneously into the BALB/c mice, which were observed for 4 days.

TABLE 11.1

Comparison of toxicity of free and particulate KGI

| Saponin (weight ratio) | ug/dose | lethargy (0-3)* | mortality (%) | liver enlargement/ darkness (0-3) | | spleen enlargement/darkness (0-3) | | gut (0-3) |
| --- | --- | --- | --- | --- | --- | --- | --- | --- |
| Free KGI 1 100% | 50 | 1.8 | 38 | 0.83 | 1.8 | 2.1 | 2.8 | (diarrhoea) 1.5 |
| KGI 1 100% | 10 | 0.0 | 0 | 0 | 0 | 0.0 | 0 | 0 |
| | 30 | 0.6 | 0 | 0.13 | 0 | 0.75 | 0.65 | 0 |
| | 50 | 0.6 | 0 | 0.12 | 0.63 | 2.0 | 1.63 | 0 |
| Free BBE 100% | 50 | 0.4 | 0 | 0 | 0.75 | 0 | 0.75 | 0 |
| | 100 | 0.7 | 0 | 0.13 | 0.5 | 1.13 | 1.62 | 0 |
| BBE 100% | 50 | 0.2 | 0 | 0 | 0 | 0 | 0.5 | 0 |
| | 100 | 1.2 | 0 | 0.24 | 0.38 | 1.5 | 0.88 | 0 |

TABLE 11.2

Scoring for degree of lethargy

| DEGREE OF LETHARGY | 0 | 1 | 2 | 3 |
| --- | --- | --- | --- | --- |
| Following people's moving | Yes, when not sleeping | no | no | no |
| When transporting the animals to an other box with fresh litter (during cleaning) they run around, and discover the new environment | immediately | slowly | very slowly or no | no |
| When suppliing them with new food, they smell it, "check" it | immediately | slowly or no | no | no |
| Mice escape, when knocking the outer wall of the box with a pencil at the site, where the mice are | immediately | slowly | no | no |
| Mice escape, when beating their bottom with a pencil | immediately | immedialey | slowly | no |
| When the tail of the animals is pressed with a forceps, causing moderate pain, they try to escape | no need for this examination | no need for this examination | immediately | very slowly or no |

Results

The effects are summarized in Table 11.1. The 10 µg dose of KGI 1 did not cause any detectable side effects in the mice. The 30 µg dose caused little reactions i.e. in a three-graded scale 0.13 liver enlargement, 0.75 spleen enlargement, 0.65 spleen darkness. The 50 µg dose of KGI 1 also caused only small changes except for spleen enlargement (2.0) and spleen darkness (1.63). It should be noted that KGI 1 has an adjuvant effect i.e. enhance immunity, and the spleen reaction is from a normal reaction. In contrast, the 50 µg dose of free form fraction C caused severe side effects including 38% mortality and high scores for lethargy (1.8), spleen enlargement (2.1), spleen darkness (2.8) and diarrhea. BBE particles are known to be virtually non-toxic and the only noticeable reaction is the spleen enlargement, which is likely due to its adjuvant effect.

Discussion and Conclusion

The systemic reaction of 50 μg of KGI 1 being close to a calculated human dose (100 μg of KGI 1) caused low degree of side effects and no mortality in 18 g BALB/c mice taking into consideration to 60 kg of a human being. In contrast, this dose (50 μg) of the free forms of the *Quillaja* fraction C being the saponin in KGI 1, caused mortality and diarrhea. A 100 μg dose of KGI 1 causes also mortality, and that should be taken into consideration that the bioavailability of the KGI 1 particle is superior to that of the fraction C. The BBE particle proved to be virtually free of side effects. The only prominent effect was the score for spleen enlargement being a reflection of its strong immune-modulating effect. Previous studies have shown that free forms of *Quillaja* saponin fractions like QS 21 and QHC cause local reactions, which is avoided by the particulate forms due to blocking effect of cholesterol tied to the saponin in the KGI and BBE particles as well as to all forms of Iscom particles. That is saponin in the mentioned particles cannot interact with the cholesterol in the cell membranes.

Example 12

Killcan establishes a new use and a new concept for cancer treatment based on the proven Iscom delivery system developed for immune stimulation. Traditional cancer killing systems are violent and causing sever side effects as the case is with cytostatica also effecting normal cells, radiation therapy also effecting normal cells and surgery with its limitations. A modern concept for cancer therapy is to interfere with the biology of replication as discussed in examples 7 and 9. Uncontrolled replication is the major driving force for most cancer forms for cancer cell survival and pathogenicity. The Killcan concept is using the well established Iscom system proven as commercial products, as a delivery system of compounds by targeting cell populations and targeting intracellular compartments such as endo- and lysosomes and the cytosol. By use of the Iscom system the Killcan concept is a driver for a normal cell development acting by modulation, activation, differentiation leading to the definite and symptomless end of the programmed cell death (apoptosis). Thus, in the present cancer therapy concept, the gained experience of the iscom technology is used, documented in 300 publications being well tested for excellent bioavailability, targeting of cells and intracellular delivery, low toxicity and other biofunctional properties. The documentation starts with the first publication by Morein et al. (Morein, 1984) to a recent and covering review (Morein, 2007).

The present analyses of the various BBE and KGI formulations were carried out by the group of Professor Rolf Lasson at Clinical Pharmacology, Uppsala University using their technology (Dhar, 1996). The killings, growth inhibiting and even synergistic effects by various combinations were indeed unexpected covering effects against cancer cells originating from myelomas, lymphomas and solid cancers. Moreover, escape mutants and cancer cells from tumors hard or impossible to treat have been sensitive to one or more of the KGI or BBE formulations, which was indeed unforeseeable.

Human Tumor Cell-Line Panel

To evaluate the activity patterns of the drugs a human cell line panel (Dhar, 1998) of four sensitive parental cell lines, five drug resistant sublines, representing different mechanisms of resistance, and one cell line with primary resistance was used. The cell lines included were the myeloma cell line RPMI 8226/S and its sublines 8226/Dox40 and 8226/LR-5 (kind gifts from W. S. Dalton, Dept of Medicine, Arizona Cancer Center, University of Arizona, Tucson, Ariz.), the lymphoma cell lines U-937 GTB and U-937-Vcr (kind gifts from K. Nilsson, Dept of Pathology, University of Uppsala, Sweden), the SCLC cell line NCI-H69 and its subline H69AR, breast cancer MCF-7 and cervix cancer Hela cell line (American Type Culture Collection; ATCC, Rockville, Md.), the renal adenocarcinoma cell line ACHN (ATCC) and the leukemic cell line CCRF-CEM and its subline CEM/VM-1 (kind gifts from W. T. Beck, Dept of Pharmacology, College of Medicine, University of Tennessee, Memphis, Tenn.).

The 8226/Dox40 was selected for doxorubicin resistance and shows the classical MDR phenotype with overexpression of P-glycoprotein 170 (Pgp). The 8226/LR-5 was selected for melphalan resistance, proposed to be associated with increased levels of GSH. The U-937-Vcr was selected for vincristine resistance, proposed to be tubulin associated. The H69AR, selected for doxorubicin resistance, expresses a MDR phenotype proposed to be mediated by MRP. The GEM/VM-1, selected for teniposide resistance, expresses an atypical MDR, which is proposed to be topoisomerase II (topoII) associated. The exact mechanism of resistance for the primary resistant ACHN cell line is not known and may be multifactoral.

The cell lines were grown in complete culture medium described in section 3.2 at 37° C. in humidified atmosphere containing 5% $CO_2$. The 8226/Dox40 was treated once a month with doxorubicin at 0.24 μg/ml and the 8226/LR-5 at each change of medium with melphalan at 1.53 μg/ml. The U-937-Vcr was continuously cultured in presence of 10 ng/ml of vincristine and the H69AR was alternately fed with drug free medium and medium containing 0.46 μg/ml of doxorubicin. The CEM/VM-1 cell line was cultured in drug free medium without any loss of resistance for a period of 6-8 months. The resistance patterns of the cell lines were routinely confirmed in control experiments.

TABLE 12.1

Human tumor cell lines used in the study

| Cell line | Origin | Selecting agent | Resistance associated with |
|---|---|---|---|
| CCRF-CEM | Leukemia | — | |
| CEM/VM-1 | " | teniposide | topoisomerase II |
| ACHN | Renal cancer | — | (primary resistance) |
| NCI-H69 | Small cell lung cancer | — | |
| H69AR | Small cell lung cancer | doxorubicin | MRP |
| RPMI 8226/S | Myeloma | — | |
| 8226/dox40 | " | doxorubicin | Pgp |
| 8226/LR5 | " | melphalan | glutathione |
| U-937 GTB | Lymphoma | — | |
| U-937-vcr | " | Vincristin | Tubulin |
| Hela | Cervix carcinoma | — | |
| MCF-7 | Breast cancer | — | |

Reagents and Drugs

A complete medium consisting of carbonate buffered culture medium RPMI-1640 (HyClone, Cramlington, UK) supplemented with 10% inactivated FCS, 2 mM glutamine, 50 μg/ml of streptomycin and 60 μg/ml of penicillin was used throughout. FDA (Sigma, St Louis, Mo.) was dissolved in DMSO and kept frozen (−20° C.) as a stock solution protected from light.

The test compounds were received from DueCom AB as 10 mM stock solutions in DMSO. Stock solutions were diluted ten times with phosphate buffered saline (PBS; Sigma Aldrich) to clear solutions. Using a BIOMEK-2000 robot system the drugs were further diluted (by ten-fold serial dilution and plated into 384-well microtiter plates (NUNC).

The Fluorometric Microculture Cytotoxicity Assay (FMCA)

Tumor cells were seeded in the drug prepared 384-well micro-titre plates at a cell density of 5,000 cells/well. The fluorometric microculture cytotoxicity assay (FMCA) is based on measurement of fluorescence generated from hydrolysis of FDA to fluorescein by cells with intact plasma membranes and has been described in detail previously [14]. The plates were incubated at 37° C. in humidified atmosphere containing 5% $CO_2$ for 72 hrs. At the end of the incubation period the was removed by aspiration. After one wash in PBS, 50 µl/well of FDA dissolved in a physiological buffer (10 µg/ml) was added. The plates were incubated for 45 minutes and the generated fluorescence from each well was measured in a 384-well scanning fluorometer. The fluorescence is proportional to the number of intact cells in the well.

Quality criteria for a successful analysis included a fluorescence signal in the control wells of more than five times mean blank value, a mean coefficient of variation (CV) in the control wells of less than 30%.

Quantification of FMCA Results

Cell survival is presented as survival index (SI), defined as the fluorescence in the experimental wells in percent of that in the control wells, with values in the blank wells subtracted.

Results

KGI and BBE formulations in different combinations killed cancer cells originating from the three categories of cancer tested i.e. lymphoma, myeloma and solid tumors. The different formulations tested covers different aspects of cancer cell killing or growth inhibition as revealed in Table 12.2.

KGI 1 had killing or growth inhibiting effect on 7 out of 11 tested cells including lymphoma, myeloma and the escape mutant of small lung cancer cell H69AR.

BBE is virtually non-toxic for normal cells tested and U937 cells used in the model described above. Unexpectedly, it was killing/growth inhibiting on the two cells i.e U937/vcr being an escape from the BBE resistant U937/GTB. More remarkable the ACHN cell was resistant to KGI 1 but sensitive to BBE and also KGI 2 also containing QHA the active component of BBE.

KGI 3 had killing or growth inhibiting effect on 6 out of the 11 tested cells. The leukemia cells were most sensitive to KGI 3 formulation. Together with KGI 2 it was the only formulation tested having effect on the breast cancer HELA cells and even potent effect when other formulations were resistant.

KGI 2 had killing or growth inhibiting effect on 5 out 11 tested cells. Together with KGI 3 it was the only one having effect and even potent effect the breast cancer HELA cells and even potent effect.

BBE/KGI 1 had killing or growth inhibiting effect on 5 out 11 tested cells. Remarkable is the potent effect on the primarily resistant ACHN cells that were resistant to KGI 1 and to the resistant myeloma cells 8226/dox40 besides these cells were also sensitive to KGI 2, but not other tested formulations.

Discussion and Conclusion

The various formulations based on the cell modulating—activating—differentiating and apoptotic properties exhibit a surprisingly broad range of cancer killing or growth inhibiting properties. In spite of the fact that the components are saponins, but not having the saponin lytic effect they have apparent complementary effects resulting that all formulations had distinct different profiles with regard to the effects on the different cancer cells tested. The total profile by the formulations tested on the killing or growth inhibition on cancer cells covered 10 out of the 11 tested cancer cell types tested. The only cell totally insensitive was the small lung cancer cell line H69. An escape mutant was sensitive to KGI 1 and KGI 3, although to limited degree.

In conclusion it unexpectedly found that a well documented system proven well accepted by normal cells has potent cancer killing or growth inhibiting properties covering a wide range of cancer types. In view of the well documented delivery properties of the cancer killing particles have the system is well suited for combination therapy either with saponin substances but also other cancer drugs preferably acting by other mechanisms, In support to this predicted effect is the capacity of the various formulations rested to escape mutants provoked by other compounds to which the cancer cells originally were sensitive.

TABLE 12.2

Killing/growth inhibition of various cancer cells expressed as IC50 (µg/ml) originating from lymphoid, myeloid and solid tumors (Table 12.1). Different effects of solitary compounds in one and the same particle i.e. BBE and KGI 1, combination of various *quillaja* saponin fractions in one particle (KGI 3), two components in one and the same particle (QHA and QHC i.e. KGI 2) and BBE particles mixed with KGI 1 in separate particles in the ratio of 4:1 BBE/KGI 1

| Cell line | Formulations | | | | |
|---|---|---|---|---|---|
| | BBE | KGI 1 | KGI 2 | KGI 3 | BBE + KGI 1 |
| U937/GTB | 100 | 0.33 | 0.34 | 0.29 | 0.36 |
| U937/vcr | 9.4 | 0.3 | 0.3 | 0.22 | 0.37 |
| CEM/S | 100 | 0.54 | 100 | 0.44 | 100 |
| CEM/R | 100 | 6 | 100 | 100 | 100 |
| H69 | 100 | 100 | 100 | 100 | 100 |
| H69AR | 100 | 27.2 | 100 | 61 | 100 |
| ACHN | 4.8 | 100 | 2.8 | 18 | 4.2 |
| 82226/S | 100 | 11.5 | 10.6 | 100 | 71 |
| 8226/dox40 | 100 | 100 | 4.8 | 100 | 4.4 |
| 8226/LR5 | 100 | 12.3 | 100 | 100 | 100 |
| HeLa | 100 | 100 | 5.5 | 5.8 | 100 |

REFERENCES

Baldridge, J. R., C. W. Cluff, at al. (2002). "Immunostimulatory activity of aminoalkyl glucosaminide 4-phosphates (AGPs): induction of protective innate immune responses by RC-524 and RC-529." *J Endotoxin Res* 8(6): 453-8.

Berendt, M. J. and J. L. Ives (1985). "Developmental status of synthetic immunomodulators." *Year Immunol:* 193-201.

Blair, A. H. and T. I. Ghose (1983). "Linkage of cytotoxic agents to immunoglobulins." *J Immunol Methods* 59(2): 129-43.

Cheng, K. T., S. E. Seltzer, et al. (1987). "The production and evaluation of contrast-carrying liposomes made with an automatic high-pressure system." *Invest Radiol* 22(1): 47-55.

Conradie, J. D., M. Govender, et al. (1983). "ELISA solid phase: partial denaturation of coating antibody yields a more efficient solid phase." *J Immunol Methods* 59(3): 289-99.

Dalsgaard (1978). "A study of the isolation and characterization of the saponin Quil A. Evaluation of its adjuvant activity, with a special reference to the application in the vaccination of cattle against foot-and-mouth disease." *Acta Vet Scand Suppl*(69): 7-40.

Dalsgaard, K. (1974). "Saponin adjuvants. 3. Isolation of a substance from *Quillaja saponaria* Molina with adjuvant activity in food-and-mouth disease vaccines." *Arch Gesamte Virusforsch* 44(3): 243-54.

Davis, M. T. and J. F. Preston (1981). "A simple modified carbodiimide method for conjugation of small-molecular-weight compounds to immunoglobulin G with minimal protein crosslinking." *Anal Biochem* 116(2): 402-7.

Dhar, S., P. Nygren, at al. (1996). "Anti-cancer drug characterisation using a human cell line panel representing defined types of drug resistance." *Br J Cancer* 74(6): 888-96.

Dhar, S., P. Nygren, et al. (1998). "Relationship between cytotoxic drug response patterns and activity of drug efflux transporters mediating multidrug resistance." *Eur J Pharmacol* 346(2-3): 315-22.

Espinet, R. G. (1951). "Nuevo tipo de vacuna antiaftosa a complejo glucovirico." Gac. Vet. 74: 1-13.

Ghose, T. I., A. H. Blair, et al. (1983). "Preparation of antibody-linked cytotoxic agents." *Methods Enzymol* 93: 280-333.

Gregoriadis, G., ed. (1984). Liposome Technology Vol. I, 29-31, 51-67 and 79-108 (CRC Press Inc., Boca Raton, Fla.)

Gregoriadis, G., B. McCormack, at al. (1999). "Vaccine entrapment in liposomes." *Methods* 19(1): 156-62.

Higuchi, R. et al. (1988). An Acylated Triterpenoid Saponin From *Quillaja saponaria*, Phytochemistry 27 (4):1165-1168.

Hope et al. (1985). Biochimica et Biophysica Acta, Vol. 812, pp. 55-65.

Hostettmann, K.; Marston, A. (1995). saponins. Cambridge, U.K.: Cambridge Univ. Press.

Johnson, A. G., M. Tomai, at al. (1987). "Characterization of a nontoxic monophosphoryl lipid A." Rev *Infect Dis* 9 Suppl 5: S512-6.

Kensil, C. R., U. Patel, et al. (1991). "Separation and characterization of saponins with adjuvant activity from *Quillaja saponaria* Molina cortex." *J Immunol* 146(2): 431-7.

Kersten, G. F., A. Spiekstra, et al. (1991). "On the structure of immune-stimulating saponin-lipid complexes (iscoms)." *Biochim Biophys Acta* 1062(2): 165-71.

Leung A Y., and Foster S. (1996). Encyclopedia of Common Natural Ingredients Used in Food, Drugs and Cosmetics, $2^{nd}$ ed., John Wiley and sons (Wiley Interscience), New York.

Lipford, G. B., H. Wagner, et al. (1994). "Vaccination with immunodominant peptides encapsulated in Quil A-containing liposomes induces peptide-specific primary CD8+ cytotoxic T cells." *Vaccine* 12(1): 73-80.

Lovgren, K. and B. Morein (1988). "The requirement of lipids for the formation of immunostimulating complexes (iscoms)." *Biotechnol Appl Biochem* 10(2): 161-72.

Lovgren, K. and B. Morein (1991). "The ISCOM: an antigen delivery system with built-in adjuvant." *Mol Immunol* 28(3): 285-6.

Lycke, N. (2004). "From toxin to adjuvant: the rational design of a vaccine adjuvant vector, CTA1-DD/ISCOM." *Cell Microbiol* 6(1): 23-32.

Ma, J., P. A. Bulger, et al. (1994). "Impact of the saponin adjuvant QS-21 and aluminium hydroxide on the immunogenicity of recombinant OspA and OspB of *Borrelia burgdorferi*." Vaccine 12(10): 925-32.

Madden, T. D., P. R. Harrigan, et al. (1990). "The accumulation of drugs within large unilamellar vesicles exhibiting a proton gradient: a survey." *Chem Phys Lipids* 53(1): 37-46.

Martin, R. G. and B. N. Ames (1961). "A method for determining the sedimentation behavior of enzymes: application to protein mixtures." *J Biol Chem* 236: 1372-9.

Mayer, L. D., M. J. Hope, et al. (1986). "Vesicles of variable sizes produced by a rapid extrusion procedure." *Biochim Biophys Acta* 858(1): 161-8.

Mayhew, E., S. Conroy, et al. (1987). "High-pressure continuous-flow system for drug entrapment in liposomes." *Methods Enzymol* 149: 64-77.

Mayhew, E., R. Lazo, et al. (1984). "Characterization of liposomes prepared using a microemulsifier." *Biochim Biophys Acta* 775(2): 169-74.

Morein, B., B. Sundquist, et al. (1984). "Iscom, a novel structure for antigenic presentation of membrane proteins from enveloped viruses." Nature 308(5958): 457-60.

Morein, B., Hu, K. of al. (2007). "New Iscoms Meet Unsettled Vaccine Demands". Vaccine Adjuvants and Delivery Systems, Chapter 9: 191-222

Mowat, A. M., A. M. Donachie, et al. (2001). "CTA1-DD-immune stimulating complexes: a novel, rationally designed combined mucosal vaccine adjuvant effective with nanogram doses of antigen." *J Immunol* 167(6): 3398-405.

O'Hagan, D T. "Recent developments in vaccine delivery systems". Curr Drug Targets Infect Disord. 2001 November; 1(3):273-86.

Ramon, G. (1926). Proc d s pour accroitre la production des antitoxines, Ann Inst Pasteur, 40, 1-10.

Rouhi A. M. (1995). Chem. Eng. News 73(37): 28-35.

Ronnberg, B., M. Fekadu, et al. (1997). "Effects of carbohydrate modification of *Quillaja saponaria* Molina QH-B fraction on adjuvant activity, cholesterol-binding capacity and toxicity." *Vaccine* 15(17-18): 1820-6.

Ronnberg, B., M. Fekadu, et al. (1995). "Adjuvant activity of non-toxic *Quillaja saponaria* Molina components for use in ISCOM matrix." *Vaccine* 13(14): 1375-82.

Stewart-Tull, D. E. (1985). "Immunopotentiating conjugates." *Vaccine* 3(1): 40-4.

Wang, Z. P. (2005). United States Patent 20050175623

Warren, H. S, and L. A. Chedid (1988). "Future prospects for vaccine adjuvants." *Crit. Rev Immunol* 8(2): 83-101.

The invention claimed is:

1. A method for the treatment of cancer wherein an iscom matrix particle comprising at least one lipid selected from cholesterol and phospholipid and at least one saponin, chosen from fraction A and fraction C from *Quillaja saponaria* Molina or a sub fraction thereof, which particle does not contain cancer antigens, is administered to an individual in need of cancer treatment.

2. The method according to claim 1, wherein the iscom matrix particle further comprises one or more saponins chosen from fraction B, fractions QA 1-22 of *Quillaja saponaria* Molina, Spicoside and Q VAC.

3. The method according to claim 1 or 2, wherein the iscom matrix particles contain at least two different saponin fractions in one and the same lipid containing particle.

4. The method according to claim 1 or 2, wherein the iscom matrix particles contain at least two different saponin fractions, whereby one of the at least two different saponin fractions is complex bound in one isco matrix particle and the other one (the other ones) of the at least two different saponin fractions is (are) complex bound in another (other) physical different lipid containing particle(s).

5. The method according to claim 1, wherein further cancer treating compounds are used together with the lipid containing particles.

6. The method according to claim 5, wherein the cancer treating compounds are chosen from platinum coordination compounds, taxane compounds, camptothecin compounds, anti-tumor *vinca* alkaloids, anti-tumor nucleoside derivatives, nitrogen mustard or nitrosourea alkylating agents, anti-tumor anthracycline derivatives, trastzumab and anti-tumor podophyllotoxin derivatives, Quila A and sub fragments thereof.

7. The method according to claim 1, wherein further adjuvants are integrated into the iscom matrix particles, coupled on to the particles or mixed with the iscom matrix particles.

8. The method according to claim 1, wherein the lipid containing particle comprises cancer targeting molecules.

* * * * *